(12) United States Patent
Uchiyama et al.

(10) Patent No.: US 8,390,679 B2
(45) Date of Patent: Mar. 5, 2013

(54) CAPSULE ENDOSCOPE DEVICE

(75) Inventors: Akio Uchiyama, Yokohama (JP); Tetsuo Minai, Hachioji (JP); Shinsuke Tanaka, Hino (JP); Takeshi Suga, Hino (JP); Tatsuya Orihara, Hachioji (JP); Kazuaki Tamura, Hachioji (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 141 days.

(21) Appl. No.: 12/964,029

(22) Filed: Dec. 9, 2010

(65) Prior Publication Data

US 2011/0273548 A1 Nov. 10, 2011

Related U.S. Application Data

(63) Continuation of application No. PCT/JP2010/059856, filed on Jun. 10, 2010.

(30) Foreign Application Priority Data

Jun. 10, 2009 (JP) ................................. 2009-139570

(51) Int. Cl.
H04N 7/18 (2006.01)
(52) U.S. Cl. ................ 348/68; 348/61; 348/65
(58) Field of Classification Search ............ 348/61, 348/65, 68
See application file for complete search history.

(56) References Cited

U.S. PATENT DOCUMENTS

| 2006/0155174 A1 | 7/2006 | Glukhovsky et al. |
| 2006/0184039 A1 | 8/2006 | Avni et al. |
| 2007/0191677 A1 | 8/2007 | Nishimura et al. |
| 2007/0221233 A1 | 9/2007 | Kawano et al. |
| 2008/0161639 A1 | 7/2008 | Katayama et al. |
| 2008/0242926 A1 | 10/2008 | Nishino |
| 2008/0242931 A1 | 10/2008 | Nishino |
| 2010/0198008 A1 | 8/2010 | Kawano |
| 2010/0204544 A1 | 8/2010 | Takei |

FOREIGN PATENT DOCUMENTS

| JP | 2004/536648 | 12/2004 |
| JP | 2005-040400 | 2/2005 |
| JP | 2005-073887 | 3/2005 |
| JP | 2006-020702 | 1/2006 |
| JP | 2006-509574 A | 3/2006 |
| JP | 2006-122502 | 5/2006 |
| JP | 2006-524097 A | 10/2006 |
| JP | 2008-237639 | 10/2008 |
| JP | 2008-237640 | 10/2008 |

(Continued)

OTHER PUBLICATIONS

International Search Report dated Jul. 13, 2010.

(Continued)

*Primary Examiner* — Allen Wong
(74) *Attorney, Agent, or Firm* — Scully Scott Murphy & Presser, PC

(57) ABSTRACT

A capsule endoscope device includes an illumination unit that illuminates a living tissue using at least one of a white light illumination unit and a special light illumination unit; an imaging unit that captures an image of the tissue; a transmission unit that transmits imaging information containing the image; a storage unit that stores a threshold with respect to information on a distance between the endoscope and the tissue; a detection unit that detects the information; and an output unit that compares the information with the threshold, selects an image capturing condition of a special light observation mode if the distance is not larger than the threshold, selects an image capturing condition of a normal light observation mode if the distance is larger than the threshold, and outputs the selected image capturing condition to an operation unit related to image capturing.

3 Claims, 23 Drawing Sheets

FOREIGN PATENT DOCUMENTS

| | | |
|---|---|---|
| JP | 2009-095566 | 5/2009 |
| WO | WO 03/011103 A2 | 2/2003 |
| WO | WO 2007/077922 A1 | 7/2007 |
| WO | WO 2007/135757 A1 | 11/2007 |
| WO | 2008/082005 A1 | 7/2008 |
| WO | WO 2008/099761 A1 | 8/2008 |
| WO | WO 2009/022667 A1 | 2/2009 |
| WO | WO 2009/069490 A1 | 6/2009 |

OTHER PUBLICATIONS

Japanese Official Action dated May 24, 2011 of corresponding Application No. JP 2010-546981 together with an English translation.
Japanese Office Action dated Jan. 25, 2011 together with an English language translation.

- 93 PHOSPHOR (PEAK IN RANGE FROM 530 nm TO 560 nm)
- 91 EXCITATION LED (PEAK IN RANGE FROM 415 nm TO 430 nm)
- 92 EXCITATION LED (PEAK IN RANGE FROM 450 nm TO 480 nm)
- 90 LED MAIN BODY

CAPSULE ENDOSCOPE DEVICE

CROSS-REFERENCE TO RELATED APPLICATIONS

This application is a continuation of PCT international application Ser. No. PCT/JP2010/059856 filed on Jun. 10, 2010 which designates the United States, incorporated herein by reference, and which claims the benefit of priority from Japanese Patent Application No. 2009-139570, filed on Jun. 10, 2009, incorporated herein by reference.

BACKGROUND OF THE INVENTION

1. Field of the Invention

The present invention relates to a capsule endoscope device that is put into a living body and acquires in-vivo images of a living tissue.

2. Description of the Related Art

In recent years, in the field of endoscopy, swallowable capsule endoscopes have been developed. Such a capsule endoscope has an image capturing function and a radio function, and has a function in which, after being swallowed by a patient for observing the body cavity, the capsule endoscope moves through the internal organs, such as the esophagus, stomach, and small intestine, by peristalsis of the internal organs and sequentially captures images until it is naturally excreted from the human body.

Japanese Laid-open Patent publication No. 2006-524097 describes an in-vivo imaging device that, during an image capturing period, turns on a light source, records the amount of light reflected to the imaging device, and controls the gain level of an image of an imaging unit.

Japanese Laid-open Patent publication No. 2005-73887 describes a radio object in-vivo information acquiring device in which a distance sensor detects the distance from the object and determines that the capsule endoscope has been swallowed into a subject when the distance is equal to or smaller than a predetermined value and then switches on a sub-switch, thereby collecting images while reducing waste power consumption.

Japanese Laid-open Patent publication No. 2006-509574 describes a system for in-vivo sensing that includes an in-vivo state tester, such as an in-vivo pH tester, and that changes the operation mode according to the in-vivo state that is acquired by the in-vivo state tester.

SUMMARY OF THE INVENTION

A capsule endoscope device according to an aspect of the present invention includes an illumination unit that includes at least a white light illumination unit that emits white light and a special light illumination unit that emits specific visible light components, the illumination unit illuminating a living tissue using at least one of the white light illumination unit and the special light illumination unit; an imaging unit that captures an image of the living tissue; a transmission unit that transmits imaging information containing the image captured by the imaging unit; a storage unit that stores a threshold with respect to information on a distance between the capsule endoscope device and the living tissue; a detection unit that detects the information on the distance between the capsule endoscope device and the living tissue; and an output unit that compares the information on the distance detected by the detection unit with the threshold, wherein the output unit selects an image capturing condition for a special light observation mode that causes only the special light illumination unit to emit light if a result of the comparing indicates that the distance to the living tissue is not larger than the threshold, the output unit selects an image capturing condition of a normal light observation mode that causes at least the white light illumination unit to emit light if the result of the comparing indicates that the distance to the living tissue is larger than the threshold, and the output unit outputs the selected image capturing condition to an operation unit that relates to image capturing.

A capsule endoscope device according to another aspect of the present invention includes an illumination means, including at least a white light illumination means for emitting white light and a special light illumination unit for emitting specific visible light components, for illuminating a living tissue using at least one of the white light illumination means and the special light illumination means; an imaging means for capturing an image of the living tissue; a transmission means for transmitting imaging information containing the image captured by the imaging means; a storage means for storing a threshold with respect to information on a distance between the capsule endoscope device and the living tissue; a detection means for detecting the information on the distance between the capsule endoscope device and the living tissue; and an output means for comparing the information on the distance detected by the detection means with a threshold, wherein the output means selects an image capturing condition for a special light observation mode that causes only the special light illumination means to emit light if a result of the comparing indicates that the distance to the living tissue is not larger than the threshold, the output means selects an image capturing condition of a normal light observation mode that causes at least the white light illumination means to emit light if the result of the comparing indicates that the distance to the living tissue is larger than the threshold, and the output means outputs the selected image capturing condition to an operation means relating to image capturing.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a capsule endoscope device according to the present invention will be described below with reference to the drawings.

Embodiment

Figure 1:
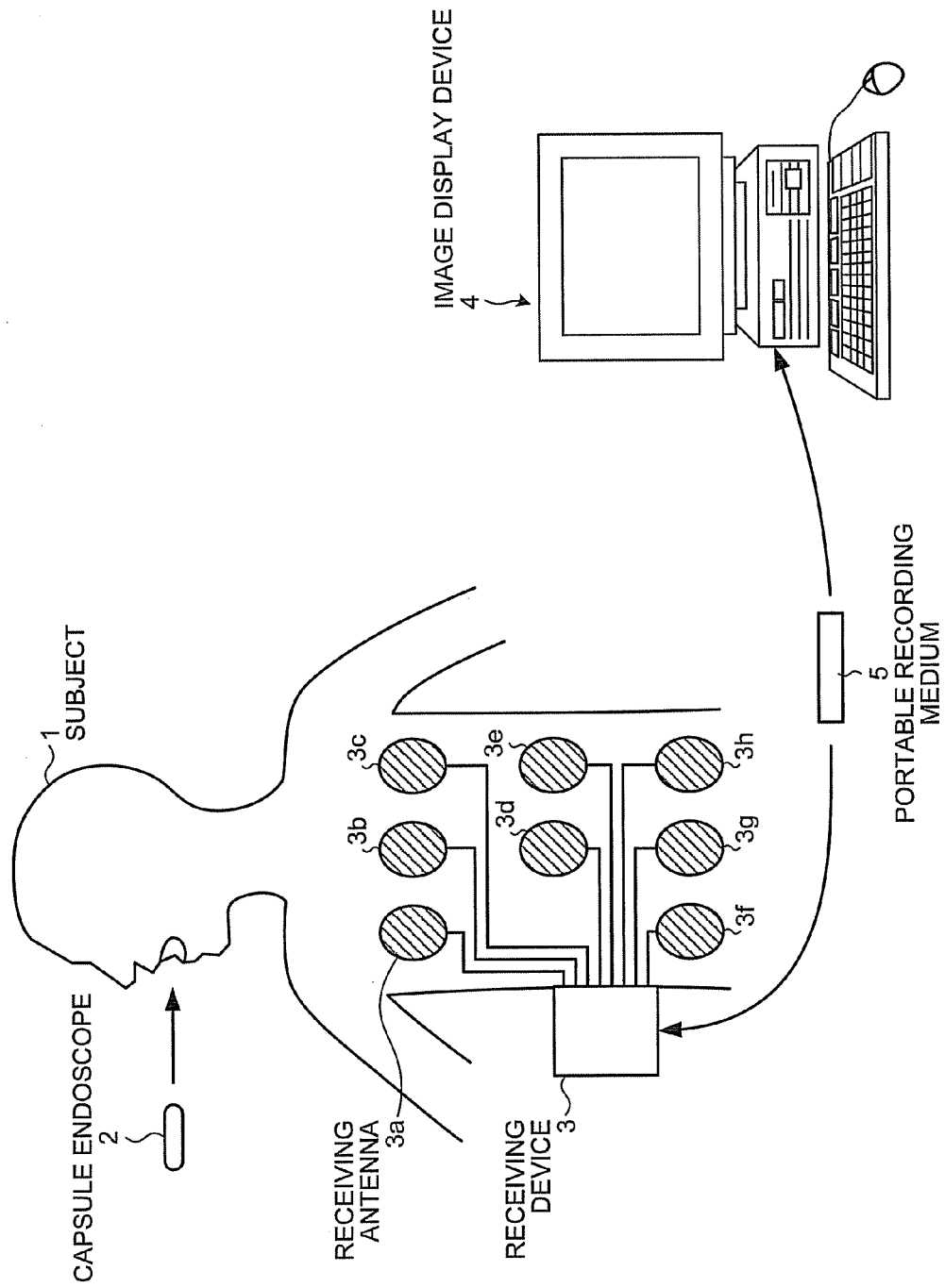
FIG. 1 is a schematic diagram of a schematic configuration of a capsule endoscope system that employs a capsule endoscope that is an embodiment of the present invention.

First, FIG. 1 is a schematic diagram of a schematic configuration of a capsule endoscope system according to an embodiment. As depicted in FIG. 1, the capsule endoscope system includes a capsule endoscope 2 that captures in-vivo images of a subject 1 and serves as a capsule endoscope device; a receiving device 3 that receives in-vivo images of the subject 1 from the capsule endoscope 2 that is introduced into the subject; an image display device 4 that displays the in-vivo images of the subject 1, which are received by the receiving device 3; and a portable recording medium 5 for receiving and transferring data between the receiving device 3 and the image display device 4.

After being swallowed by the subject 1, the capsule endoscope 2 sequentially captures in-vivo images of the subject 1 while moving through the internal organs of the subject 1 by, for example, peristalsis. Each time the capsule endoscope 2 captures in-vivo images of the subject 1, the capsule endoscope 2 sequentially transmits by radio imaging information containing the captured images to the receiving device 3 outside. In this case, the capsule endoscope 2 sequentially transmits each in-vivo image of the subject 1 at time intervals corresponding to unique functions of the capsule endoscope 2.

The receiving device 3 receives the group of in-vivo images of the subject, which are captured by the capsule endoscope 2, and stores the received in-vivo image group. Specifically, the receiving device 3 includes a plurality of receiving antennae 3a to 3h. The receiving antennae 3a to 3h are attached to the subject 1 having internal organs to which the capsule endoscope 2 is introduced, or the subject 1 carries the receiving antennae 3a to 3h. The receiving device 3 sequentially receives the imaging information, which is transmitted by the capsule endoscope 2 in the subject 1, via the receiving antennae 3a to 3h and thus acquires the group of in-vivo images of the subject 1. The receiving device 3 includes the portable recording medium 5, which is detachably attached, and records the group of in-vivo images of the subject 1, which is acquired from the capsule endoscope 2, in the portable recording medium 5.

The receiving antennae 3a to 3h are separately arranged, for example, along the path in which the capsule endoscope 2, which is introduced into the internal organs of the subject 1, moves (the digestive canal of the subject 1) on the body surface of the subject 1 and are connected to the above-described receiving device 3. The receiving antennae 3a to 3h capture the imaging information, which is transmitted by the capsule endoscope 2 in the subject 1, and sequentially transmits the captured imaging information to the receiving device 3. The receiving antennae 3a to 3h may be separately arranged on a jacket that the subject 1 wears. It is sufficient if one or more receiving antennae that capture the imaging information be arranged on the subject 1. The number of receiving antenna is not limited to eight.

The image display device 4 has a configuration like that of a work station that acquires various types of data, such as a group of in-vivo images of the subject 1, via the portable recording medium 5 and displays the acquired various types of data on the display. Specifically, the portable recording medium 5, which records the group of in-vivo images of the subject 1, is detachably attached to the image display device 4, and the image display device 4 loads the group of in-vivo images of the subject 1 from the attached portable recording medium 5. In this case, the image display device 4 acquires the group of in-vivo images that are identified by the receiving device 3 according to each function unique to the capsule endoscope 2. The image display device 4 sores and manages the group of in-vivo images, which is acquired as described above, according to each function unique to the capsule endoscope 2 and displays each in-vivo image being distinguished according to each function unique to the capsule endoscope 2. Because the image display device 4 distinguishes and displays each in-vivo image of the subject 1, a user, such as a doctor or a nurse, can observe (examine) each in-vivo image of the subject 1 easily and efficiently. The user diagnoses the subject 1 by observing each in-vivo image of the subject 1 that is displayed by the image display device 4.

The portable recording medium 5 is a recording medium that can be carried and is used for receiving and transferring data between the receiving device 3 and the image display device 4. Specifically, the portable recording medium 5 is configured to be attachable to and detachable from the receiving device 3 and the image display device 4 and to output and record data when it is attached to the receiving device 3 and the image display device 4. When being attached to the receiving device 3, the portable recording medium 5 records the group of in-vivo images of the subject 1, which are received by the receiving device 3 from the capsule endoscope 2. When being attached to the image display device 4, the portable recording medium 5 sends the recorded data, such as the group of in-vivo images of the subject 1, to the image display device 4.

The various types of data that the portable recording medium 5 records are, for example, the group of in-vivo images of the subject 1, time information (image-capturing time, receiving time) regarding each in-vivo image of the in-vivo image group, patient information on the subject 1, examination information on the subject 1, and image capturing mode information. The patient information on the subject 1 is specific information that specifies the subject 1, such as the patient name, date of birth, sex, age. The examination information on the subject 1 is specific information that specifies the examination for observing the internal organs by introducing the capsule endoscope 2 into the internal organs, such as the examination ID and examination date. The image capturing mode information is information representing an image capturing mode during image capturing that is a normal light observation mode or a special light observation mode, which will be described below.

Figure 2:
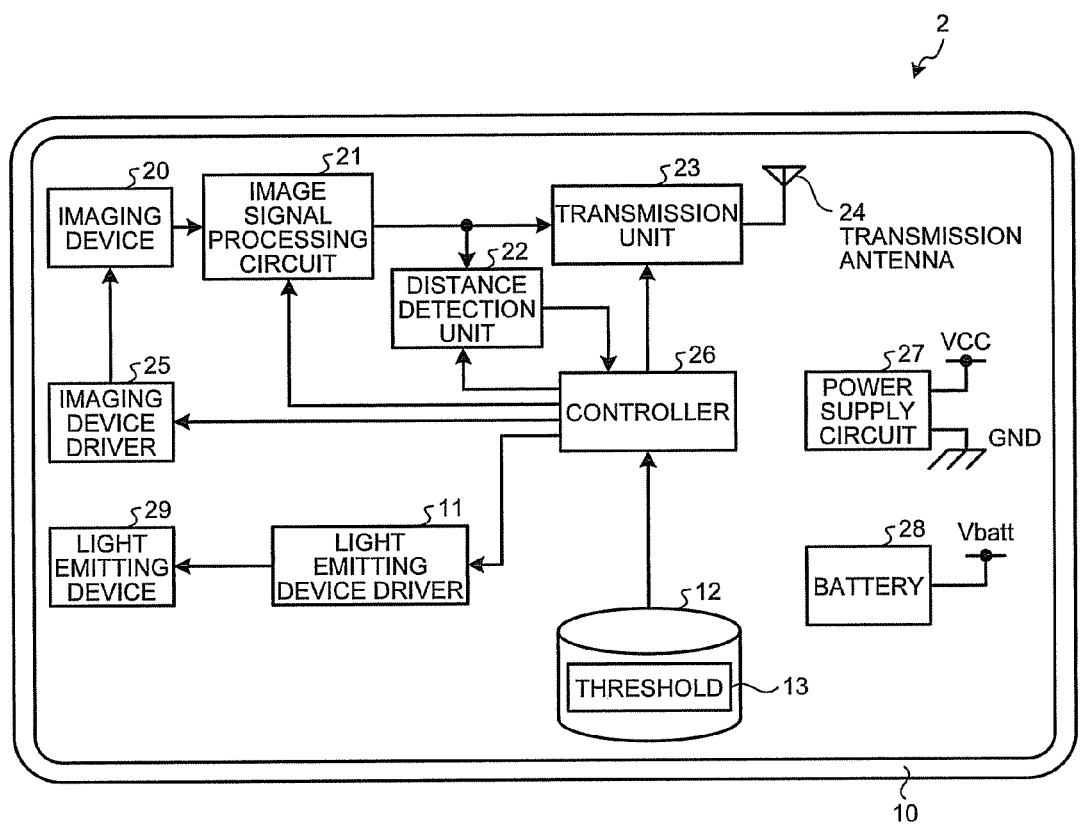
FIG. 2 is a block diagram of a configuration of the capsule endoscope in FIG. 1.

FIG. 2 is a block diagram of a configuration of the capsule endoscope 2. The capsule endoscope 2 is covered with a casing 10. The casing 10 has a shape like a capsule, which is formed in a size such that it can be easily introduced into the subject 1, and is formed of a casing main body 10a and an optical dome 10b (see FIG. 4). The casing main body 10a is a casing member having a cylindrical structure with one open end and the other closed end like a dome. The optical dome 10b is a transparent optical member formed into a shape like a dome. The optical dome 10b is attached to the casing main body 10a such that that the optical dome 10b seals the open end, which is one end of the casing main body 10a. The casing 10 formed of the casing main body 10a and the optical dome 10b houses each element of the capsule endoscope 2 in a watertight manner.

The capsule endoscope 2 includes a light emitting device 29, which is realized using multiple LEDs, and a light emitting device driver 11 that drives and controls each light emitting device of the light emitting device 29. The light emitting device 29 and the light emitting device driver 11 serve as an illumination unit. The capsule endoscope 2 further includes an imaging device 20 that is a solid-state imaging device realized using a CCD or a CMOS; an imaging device driver 25 that drives and controls the imaging device 20; and an image signal processing circuit 21 that processes pixel signals, which are output from the imaging device 20, as an image signal. The imaging device 20, the imaging device driver 25, and the image signal processing circuit 21 serve as an imaging unit. A transmission unit 23 outputs the imaging information containing image information, which is output from the image signal processing circuit 21, as a radio signal from a transmission antenna 24.

A distance detection unit 22 detects information on the distance between the object and the capsule endoscope 2 on the basis of the image information, which is output from the image signal processing circuit 21, or information from a controller 26. The controller 26 generally controls the capsule endoscope 2. The controller 26 determines the next image capturing mode by comparing the information on the distance, which is detected by the distance detection unit 22, with a threshold 13 about switching between image capturing modes stored in a storage unit 12, and the controller 26 controls the imaging device driver 25 and/or the light emitting device driver 11 such that an imaging process in the determined image capturing mode is performed. The image-capturing mode includes the normal light observation mode and the special light observation mode. The capsule endoscope 2 includes a battery 28, which is realized using a cell battery, and a power supply circuit 27 that supplies power to each element using the battery 28.

Figure 3:
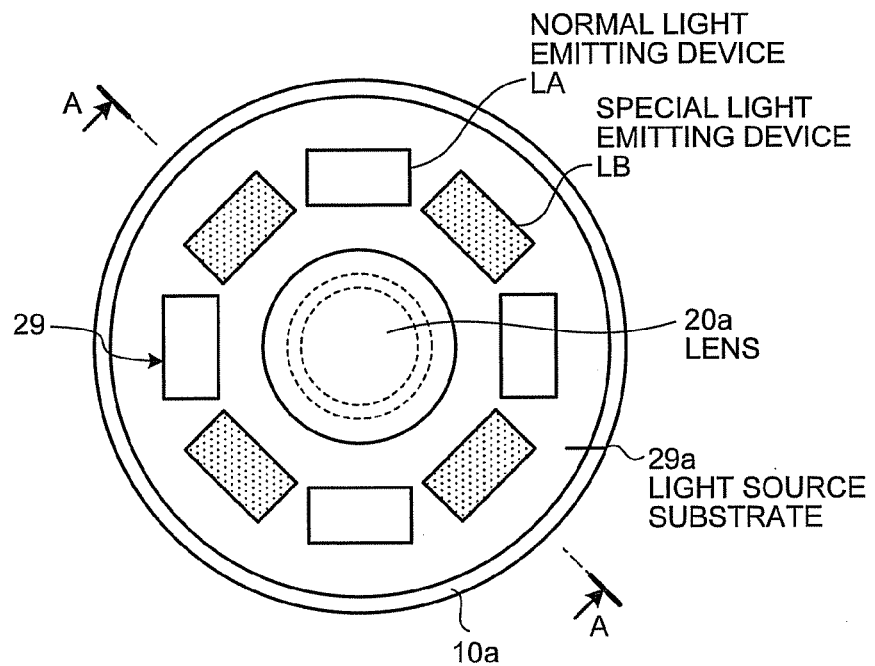
FIG. 3 is a diagram of an arrangement of light emitting devices in the capsule endoscope in FIG. 1.
Figure 4:
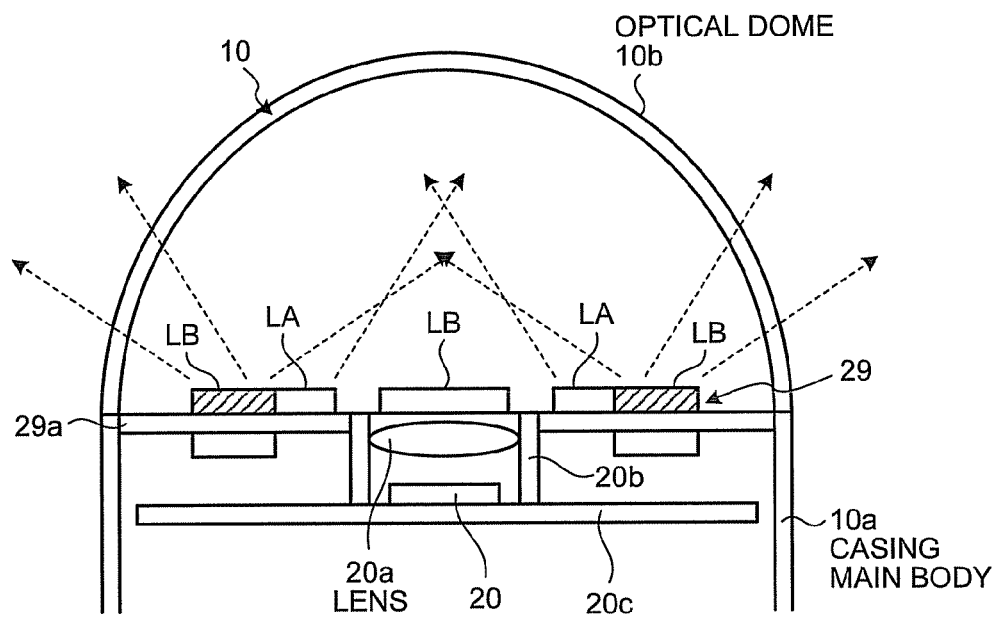
FIG. 4 is a cross-sectional view taken along the line A-A in FIG. 3.
Figure 5:
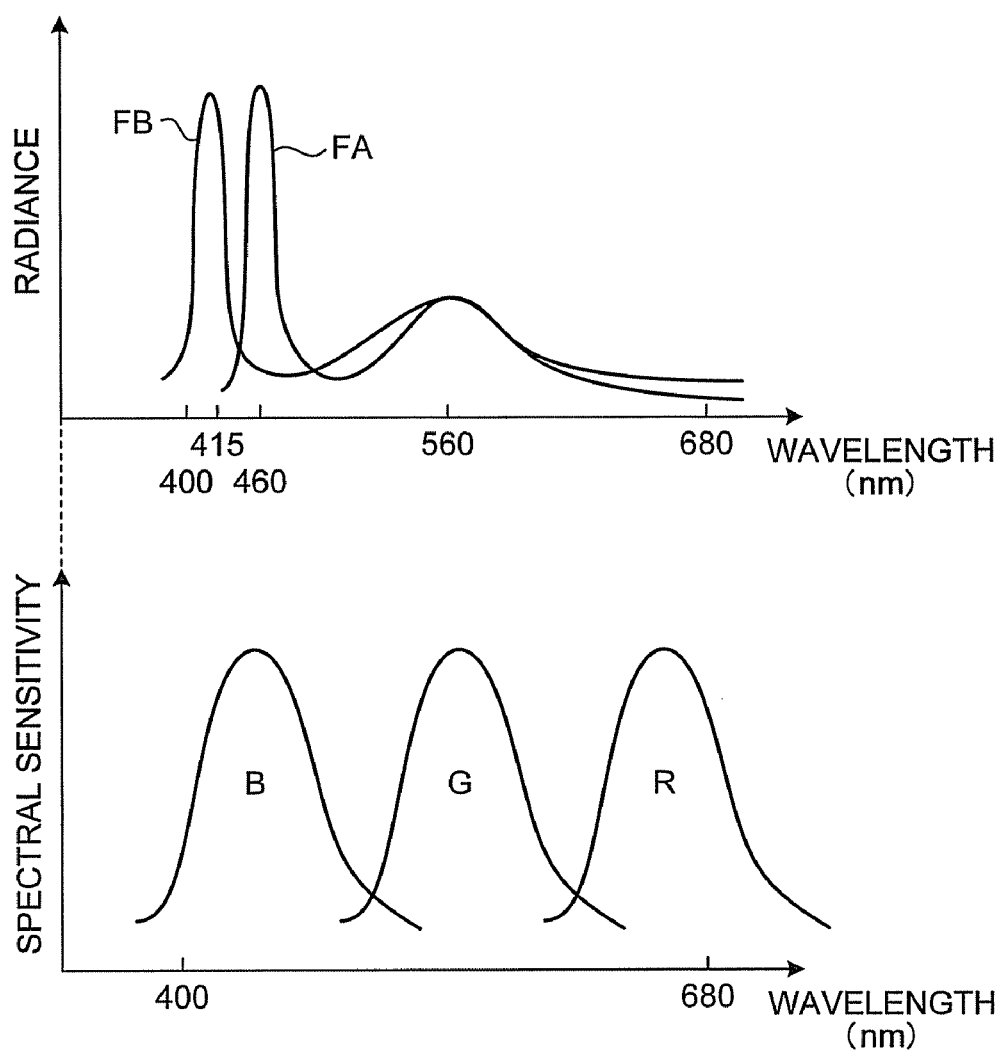
FIG. 5 is a graph of an example of the radiance spectrum of a light emitting device and the spectral sensitivity spectrum of the imaging device in the capsule endoscope in FIG. 1.

A detailed configuration of the illumination unit and the imaging unit will be described. FIG. 3 is a diagram of an arrangement of optical devices of the light emitting device 29 in the capsule endoscope, viewed from the side of the optical dome. FIG. 4 is a vertical cross-sectional view of a portion in which the illumination unit and the imaging unit are arranged and its neighboring portion, and FIG. 4 corresponds to a cross-sectional view taken along the line A-A in FIG. 3. FIG. 5 is a graph of wavelength dependence of radiance of the light emitting device and wavelength dependence of spectral sensitivity of the imaging device 20. As depicted in FIGS. 3 and 4, the light emitting device 29 includes two types of light emitting devices that are alternately arranged annularly around the imaging device 20 and a lens 20a. The two types of light emitting devices are made up of four normal light emitting devices LA and four special light emitting devices LB and are arranged on a light source substrate 29a.

The normal light emitting device LA is a white light source in which a yellow phosphor is provided on a blue LED having a peak wavelength in a range from about 450 nm to about 480 nm, preferably a peak wavelength of about 460 nm. The normal light emitting device LA has the radiance distribution represented by the curve FA in FIG. 5. In contrast, the special light emitting device LB is a white light source in which a yellow phosphor is provided on a blue LED having a peak wavelength, shorter than that of the blue LED of the normal light emitting device LA, in a range from about 415 nm to about 430 nm, preferably a peak wavelength of about 415 nm. The normal light emitting device LB has the radiance distribution represented by the curve FB in FIG. 5. The yellow phosphor emits fluorescent light having a peak in a range from about 530 nm to about 560 nm according to the wavelength of light emitted by each blue LED. The normal light emitting device LA is realized as a normal white light source. The special light emitting device LB is also a white light source, but the peak wavelength of the radiance is around 415 nm. Blue light around 415 nm has features that blue light is easily absorbed by hemoglobin, thus is not reflected by a bleeding site and is reflected in a non-bleeding site, and that, in a shallow portion below the surface of the living body, blue light is absorbed in a blood vessel in the shallow portion. Thus, by processing an image, which is obtained using irradiation by the special light emitting device LBs, special observation can be performed in which blood-absorbed light image clearly representing a bleeding site is obtained. In this embodiment, in the normal light observation mode, both of the normal light emitting devices LA and the special light emitting devices LB are caused to emit light. In the special light observation mode, only the special light emitting devices LB are caused to emit light.

As depicted in FIG. 4, the special light emitting device LB has light distribution characteristics of an orientation angle equal to or more than 60 degrees, which is broader than that of the normal light emitting device LA. This is because, in the special light observation mode, an object close the capsule endoscope 2 is observed widely, and, in the normal light observation mode, an object separated from the capsule endoscope 2 is observed. The lens 20a that is positioned at the center of the longitudinal axis of the capsule endoscope 2 is arranged on the top part of the imaging device 20 in a lens barrel 20b. The lens 20a focuses the light, which is applied from the light emitting device 29 and reflected from the object, and forms an image on the imaging device 20. The lens barrel 20b and the imaging device 20 are arranged and fixed on an image-capturing substrate 20c. The imaging device 20 includes RGB color filters in a Bayer arrangement and has the spectral sensitivity wavelength dependence corresponding to the characteristics of each of the RGB color filters.

Figure 6:
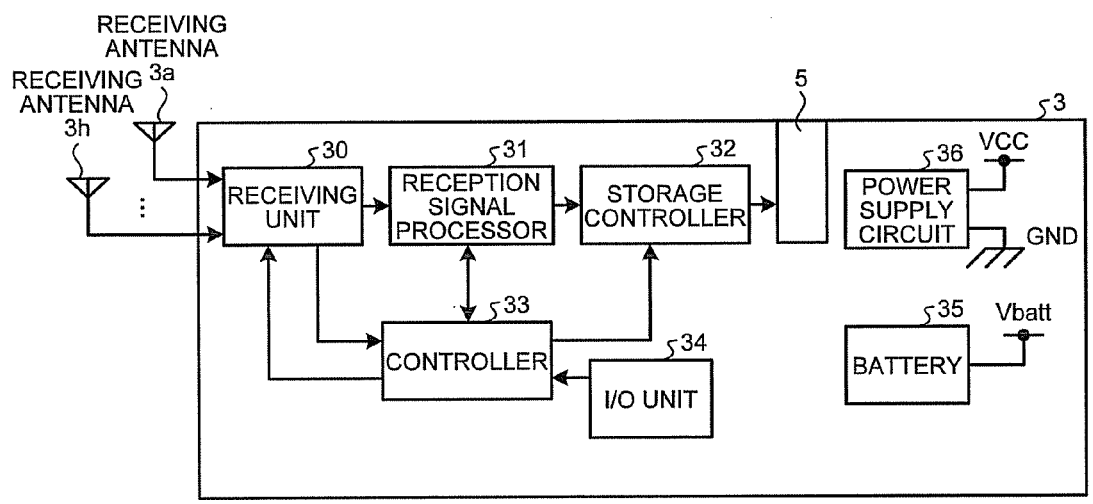
FIG. 6 is a block diagram of a configuration example of a receiving device in the capsule endoscope system in FIG. 1.

As illustrated in FIG. 6, the receiving device 3 decodes RF signals that are received by the receiving antennae 3a to 3h, and a reception signal processor 31 generates image information on the basis of the decoded signals and stores the image information in the portable recording medium 5 via a storage controller 32. A controller 33 generally controls the receiving device 3. The controller 33 selects a receiving antenna having the highest receiving electric field intensity from the receiving antennae 3a to 3h on the basis of the receiving electric field intensity of an RF signal, which is received by a receiving unit 30, and outputs an instruction for switching the receiving antenna to the receiving unit 30. An I/O unit 34 inputs or outputs various types of instruction information. The I/O unit 34 is realized using, for example, a touch panel. The receiving device 3 includes a battery 35 that is realized using a cell battery and includes a power supply circuit 36 that supplies power to each element using the battery 35.

Figure 7:
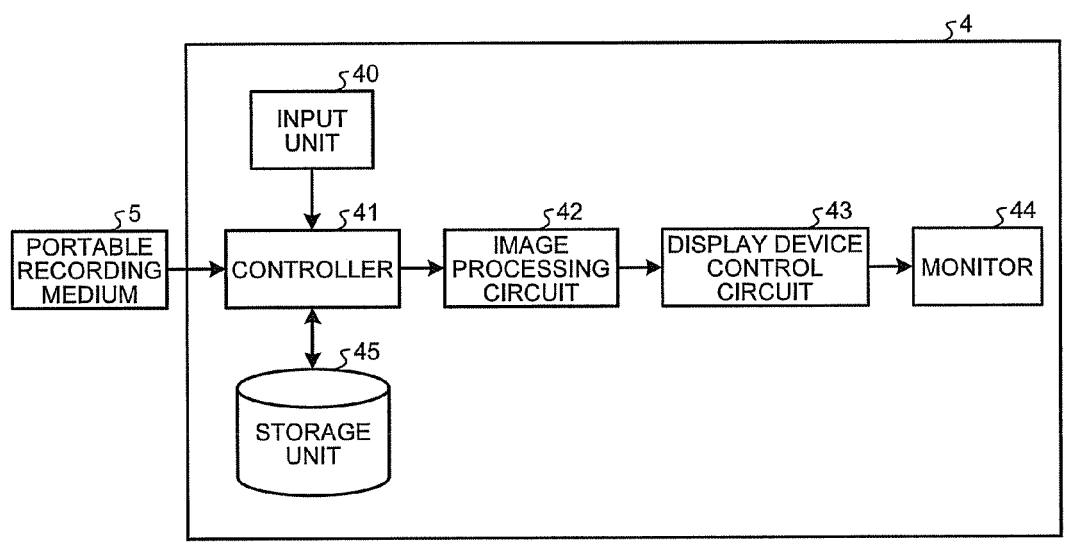
FIG. 7 is a block diagram of a configuration example of an image display device in the capsule endoscope system in FIG. 1.

FIG. 7 is a block diagram of a configuration of the image display device 4. As depicted in FIG. 7, a controller 41 of the image display device 4 acquires imaging information that is input from the portable recording medium 5 and stores the imaging information in a storage unit 45 according to an instruction from an input unit 40. Thereafter, according to an instruction from the input unit 40, the controller 41 loads a desired image stored in the storage unit 45 and outputs and displays the image on a monitor 44 via a display device control circuit 43 after an image processing circuit 42 performs desired image processing on the image.

Figure 8:
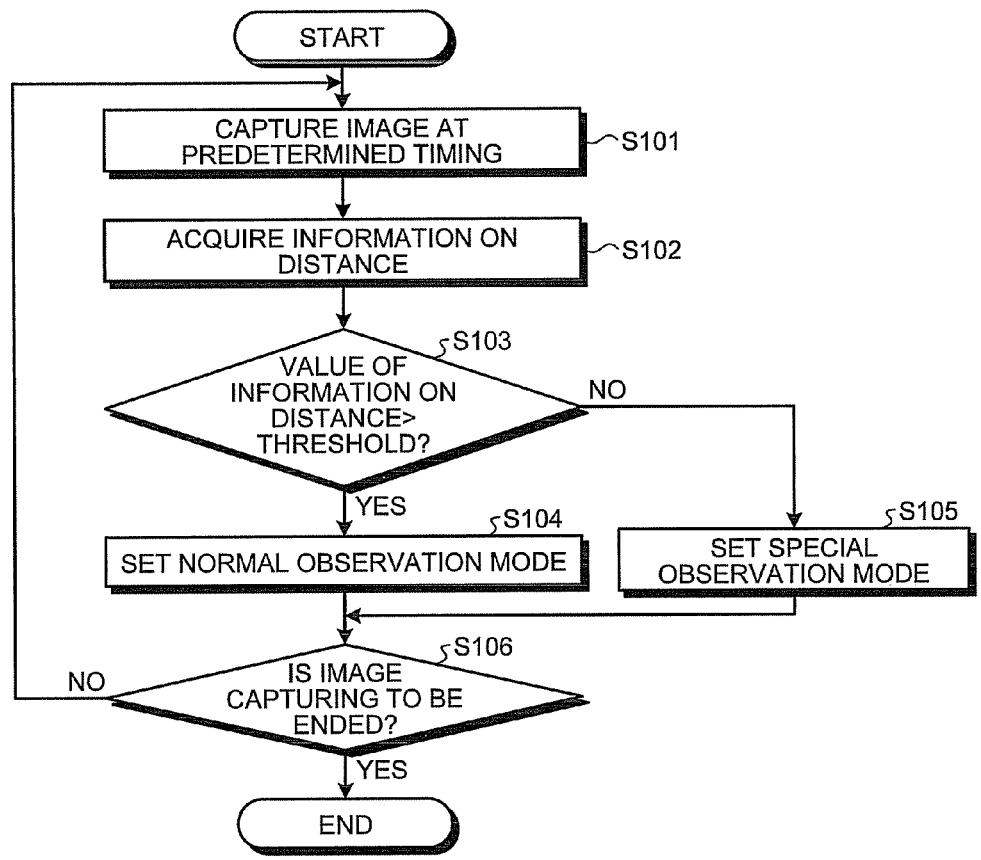
FIG. 8 is a flowchart of a procedure of a process for switching between image capturing modes, which is performed by a controller in the capsule endoscope in FIG. 1.

A procedure of an image capturing mode switching setting process performed by the capsule endoscope 2 will be described here with reference to the flowchart in FIG. 8. In FIG. 8, first, the controller 26 controls the imaging device driver 25 and the light emitting device driver 11 to perform an imaging process at a predetermined timing, for example, at every 0.5 second (step S101). The distance detection unit 22 then acquires information on the distance on the basis of the acquired imaging information or information from the controller 26 (step S102). Thereafter, the controller 26 determines whether the value of the information on the distance, such as the light emitting time, is larger the threshold 13 (step S103). When the value of the information on the distance is larger than the threshold 13 (YES at step S103), because the object and the capsule endoscope 2 are distant from each other, the controller 26 sets the image capturing mode to the normal light observation mode (step S104) and goes to step S106. In contrast, when the value of the information on the distance is not larger than the threshold 13 (NO at step S103), because the object and the capsule endoscope 2 are close to each other, the controller 26 sets the image capturing mode to the special light observation mode (step S105), and goes to step S106. At step S106, the controller 26 determines whether to end the imaging process. When the imaging process is not to be ended (NO at step S106), the controller 26 goes to step S101 and repeats the above-described imaging process in the imaging mode, which is set at step S104 or step S105. When the imaging process is to be ended (YES at step S106), the controller 26 ends the process. As described above, in the normal light observation mode, both of the normal light emitting devices LA and the special light emitting devices LB are caused to emit light and an image is captured. In the special light observation mode, only the special light emitting devices LB are caused to emit light and an image is captured. At least information representing the imaging mode is added to the imaging information, which is captured as described above, and then the imagining information is transmitted to the receiving device 3.

Information on Distance: Light Emitting Time

A specific example of the information on the distance will be described here. The controller 26 performs an automatic light adjustment control according to the acquired image information. The automatic light adjustment control adjusts the time during which the light emitting device 29 (LED) emits light. When the capsule endoscope 2 and the object are distant from each other, because the amount of light reflected from the object is small and thus it is dark, the time during which the light emitting device 29 emits light is adjusted to be longer. When the capsule endoscope 2 and the object are close to each other, because the amount of light reflected from the object is large, the time during which the light emitting device 29 emits light is adjusted to be shorter. In other words, by detecting the time during which the light emitting device 29 emits light, the distance between the capsule endoscope 2 and the object can be detected.

Figure 9:
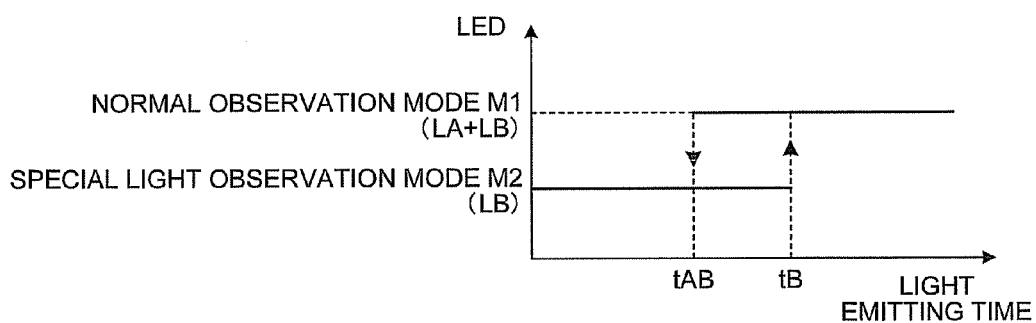
FIG. 9 is a graph of an example in which the capsule endoscope device of the present invention switches between the image capturing modes according to the time during which the light emitting device emits light.

As depicted in FIG. 9, when the currently-set image capturing mode is a special light observation mode M2, the controller 26 determines whether the light emitting time exceeds a threshold tB. When the light emitting time exceeds the threshold tB, the controller 26 performs a process of changing the setting to the normal light observation mode M1. In contrast, when the image capturing mode is a normal light observation mode M1, the controller 26 determines whether the light emitting time is less than a threshold tAB. When the light emitting time is less than the threshold tAB, the controller 26 performs a process of changing the setting to the special light observation mode M2. In this example, in order to prevent contact bounce, the thresholds tAB and tB different from each other are used. Alternatively, the thresholds tAB and tB may be the same. In addition, in this example, the value of the drive current to each of the normal light emitting device LA and the special light emitting device LB is the same.

Information on Distance: Brightness of Image

Figure 10:
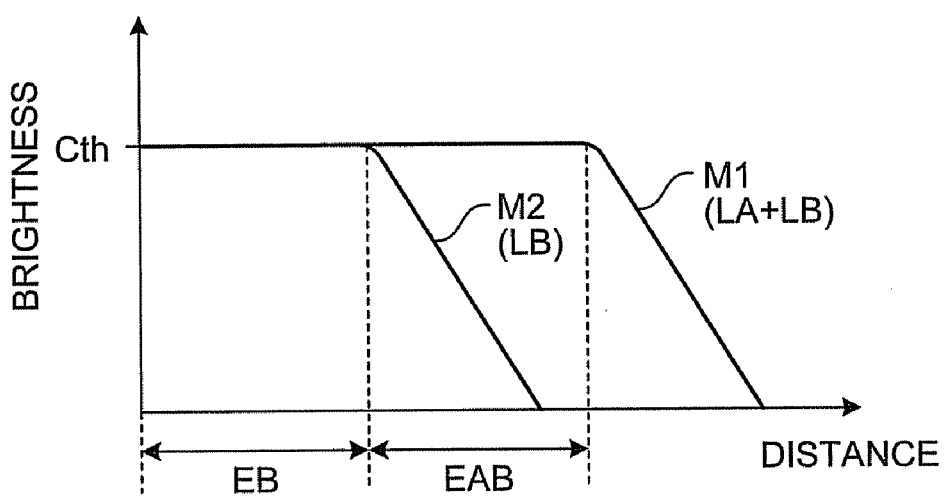
FIG. 10 is a graph of distance dependence of brightness of an image, which is captured by the capsule endoscope in FIG. 1, in each image capturing mode.

A case in which the brightness of an image is detected as the information on the distance will be described below. The pixel average value of a high luminance portion in the acquired image is used as the brightness of the image. As represented in FIG. 10, with an increase in the distance between the capsule endoscope 2 and the object, the pixel average value of the high luminance portion is out of the saturated state at a certain distance and then decreases. Thus, when the currently-set image capturing mode is the special light observation mode M2 and the brightness of the image decreases to be less than a threshold Cth, the controller 26 changes the setting to the normal light observation mode M1. In other words, in the special light observation mode M2, for an area EAB in which the brightness is less than the threshold Cth, the controller 26 changes the setting to the normal light observation mode M1.

Here, for an area EB in which the threshold is Cth in both of the normal light observation mode M1 and the special light observation mode M2, when the normal light observation mode M1 is currently set, only the special light emitting devices LB are caused to emit light in advance and the brightness is detected. When the brightness is less than the threshold Cth, the normal light observation mode M1 is maintained. When the brightness is at the threshold Cth, it is preferable to change the setting to the special light observation mode M2 in view of power saving.

Figure 11:
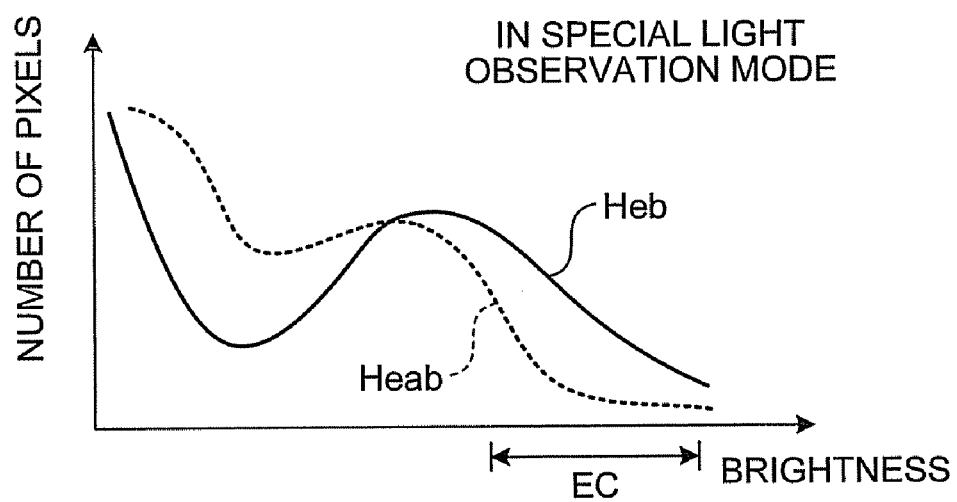
FIG. 11 is a graph of an example of the relation between the brightness distribution of each pixel in an image, which is captured by the capsule endoscope in FIG. 1 in the special light observation mode, and the imaging distance.

Instead of the pixel average value of the high luminance portion, a distribution curve of brightness of each pixel may be obtained as depicted in FIG. 11 and, according to variations in the shape of a high luminance portion EC of the distribution curve, the distance between the capsule endoscope 2 and the object may be detected. For example, a curve Heb varies to a curve Heab with an increase in the distance. The distance may be detected from variations in the whole shape of the distribution curve.

Figure 12:
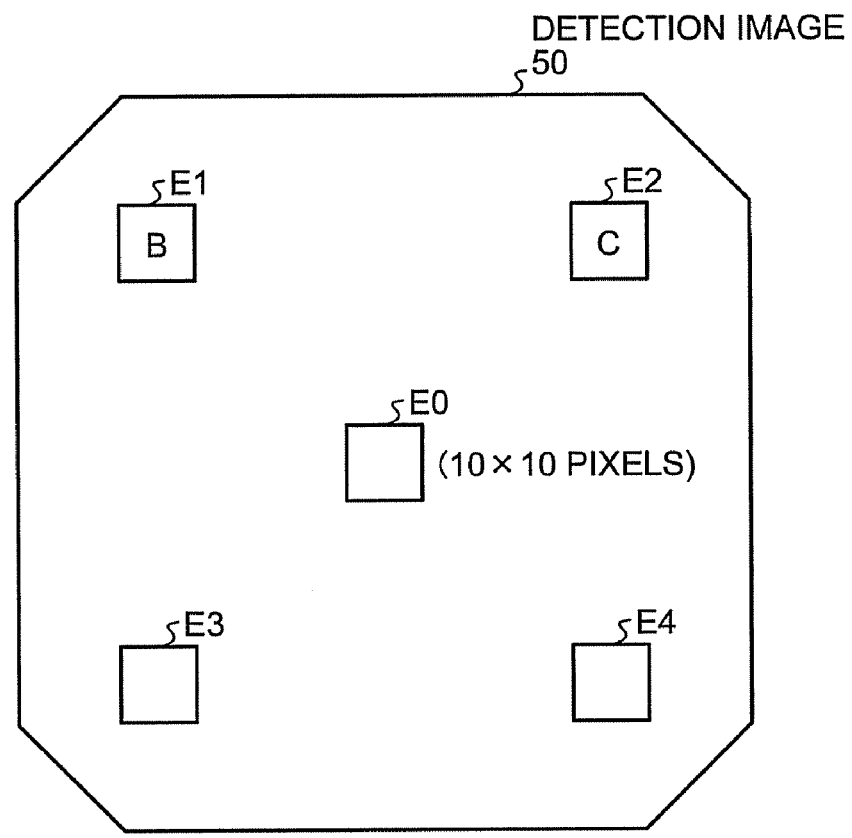
FIG. 12 is a diagram of an example of a distribution of pixels whose brightness is to be detected when the capsule endoscope device of the present invention detects the brightness of an image.

As depicted in FIG. 12, the brightness not of the whole pixels of a detection image but of a part of the pixels may be detected. In FIG. 12, the distance detection unit 22 obtains the brightness of each of areas E0 to E4, including an area E0 at the center portion in a detection image 50 and four areas E1 to E4 in peripheral portions. Each of the areas E0 to E4 is an area of 10×10 pixels and the luminance is obtained as brightness. In other words, brightness $Y=0.11 \cdot B+0.59 \cdot G+0.30 \cdot R$ is obtained. The brightness may be obtained from, instead of the luminance, only red (R) components having the least absorbance characteristics in the body.

Information on Distance: Lumen Detection

In this case, because the area E0 of the center portion and the areas E1 to E4 of the peripheral portions are detected, it can be detected whether an image is captured in the axial direction of the lumen. In other words, when the brightness of the area E0 is less than a predetermined value A and the brightness of the areas E1 to E4 exceeds a predetermined value B, it can be determined that the image is captured in the axial direction of the lumen. When the image is captured in the axial direction of the lumen, it is preferable that setting be changed to the normal light observation mode M1. By adding this image capturing condition for the process of switching the image capturing mode, the fine witching process can be performed.

Information on Distance: Space Frequency of Image

Figure 13:
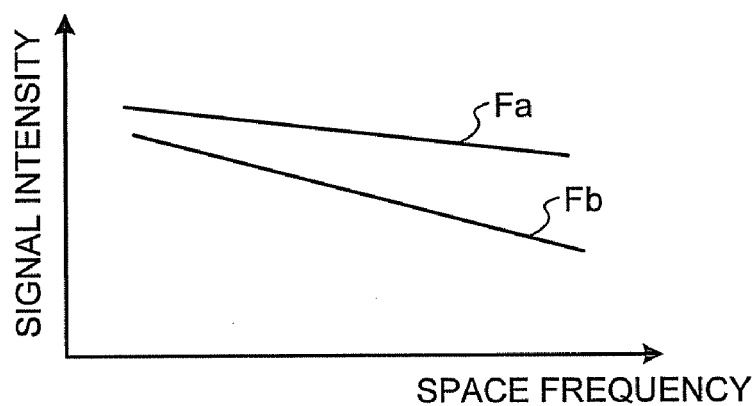
FIG. 13 is a graph of an example of the relation between the space frequency dependence of the signal intensity of an image, which is captured by the capsule endoscope of the present invention, and the imaging distance.

A case in which the space frequency of an image is detected as the information on the distance will be described. The acquired image has large irregularities if the distance to the object is large and has small irregularities if the distance to the object is small. In other words, as represented in FIG. 13, in both of the case in which the distance to the object is small and the case in which the distance is large, the signal intensity of an image signal decreases as the space frequency increases, but the reduction represented by the curve Fb in the case of the large distance is larger and thus the difference between the signal intensity of the curve Fb and that of a curve Fa in the case of the small distance increases.

In other words, the distance detection unit 22 can detect the distance by obtaining the space frequency distribution. The space frequency distribution is realized using FFT (Fast Fourier Transform) in which one-dimensional or two-dimensional processing is performed. When one-dimensional FFT processing is performed, multiple lines may be averaged. If the color filter has a Bayer arrangement, it is preferable that the space frequency of pixels of G components be obtained. This is because two of four pixels are of G components in the Bayer arrangement and thus the space frequency can be acquired accurately.

Information on Distance: Contact Detection

Figure 14:
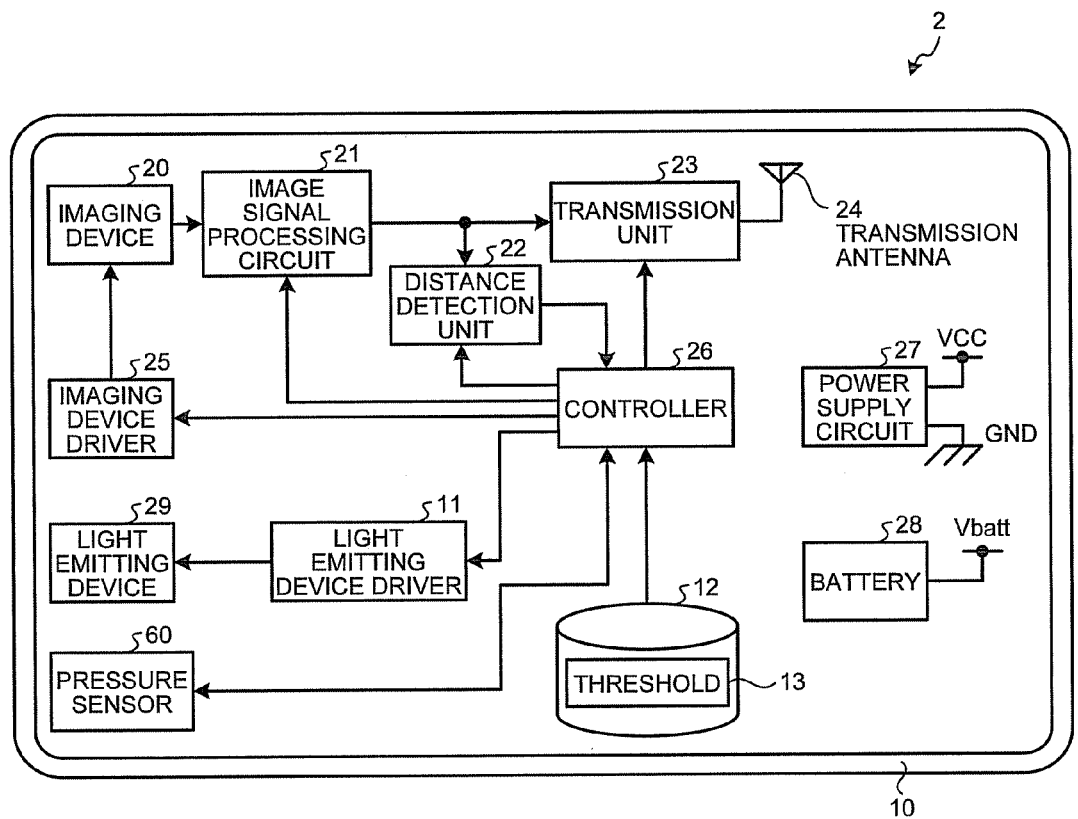
FIG. 14 is a diagram of a configuration example of the capsule endoscope in FIG. 2 to which a pressure sensor is added.
Figure 15:
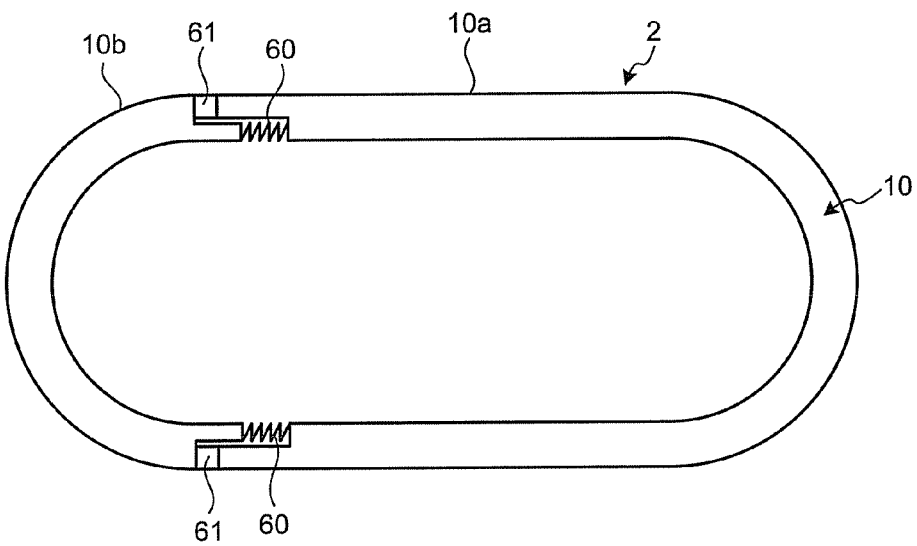
FIG. 15 is a diagram of an example of specific arrangement of the pressure sensor in FIG. 14.

Here, the distance is detected according to whether the optical dome 10b makes a contact with the object. As depicted in FIG. 14, the capsule endoscope 2 is provided with a pressure sensor 60 and the distance detection unit 22 detects a contact with the object by receiving the result of measurement by the pressure sensor 60 from the controller 26. As depicted in FIG. 15, the pressure sensor 60 is provided to a connection portion between the optical dome 10b and the casing main body 10a. An elastic member 61 is provided between the optical dome 10b and the casing main body 10a and thus the optical dome 10b is movable toward the casing main body 10a in the longitudinal direction. The pressure sensor 60 includes a pressing member having, for example, a shape like a spring. The pressure sensor 60 is realized using a MEMS (micro-electro-mechanical systems) device. When the optical dome 10b makes a contact with, for example, the wall of the digestive canal, the pressure sensor 60 compresses due to the pressing and the pressure is detected by detecting the deformation electrically or mechanically.

When the pressure measured by the pressure sensor 60 exceeds the threshold 13, the distance detection unit 22 determines that the optical dome 10b makes a contact with the object and detects that the distance between the object and the capsule endoscope 2 is small. When the distance is small, the controller 26 sets the special light observation mode M2. When the distance is large, the controller 26 sets the normal light observation mode M1.

The controller 26 may increase the luminance intensity by the light emitting device 29 when the optical dome 10b makes a contact with the object, and the capsule endoscope 2 may further be provided with a contact image capturing mode M3 with much shorter exposure time. In the contact image capturing mode M3, a small light absorption reaction of hemoglobin can be captured in an image without fail by increasing the luminance intensity, and the output of the imaging device 20 can be prevented from being saturated by shortening the exposure time in accordance with the increase in the luminance intensity.

Figure 16:
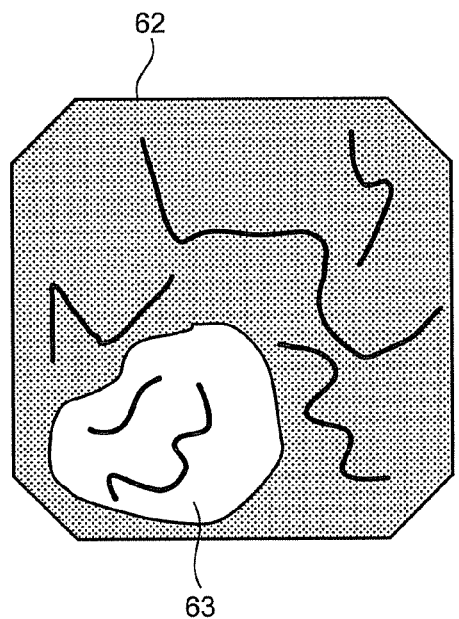
FIG. 16 is a diagram schematically illustrating an example of an image that is captured by the capsule endoscope in FIG. 1 with its optical dome making a contact with an in-vivo tissue.

As depicted in FIG. 16, it is preferable that image processing for changing the level of highlighting the structure be performed on a portion 63 with which the optical dome 10b makes a contact in an acquired image 62. By performing such image processing, blood capillaries on the surface of the digestive canal can be highlighted and displayed. Detection of the contact portion 63 can be realized by detecting a portion having brightness equal to or more than a certain value, having evenness, and having a space frequency component lower than that of peripheral areas, i.e., a portion with small irregularities.

Information on Distance: Contact Detection by Color Component Detection

When the small intestine is observed, the image is yellow due to bilirubin. On the other hand, when the optical dome 10b makes a contact with a living tissue, the bilirubin is pushed out from the imaging area and thus the yellow components are reduced. The information on the yellow components is contained in the information on the G pixels and R pixels. Thus, for example, when the ratio B/G of the signal intensity of the G with respect to the signal intensity of the B pixels is obtained and the ratio B/G exceeds a threshold, it can be determined that the optical dome 10b makes a contact with the living tissue. This is because, when a contact is made, B of the ratio does not change and G of the ratio becomes small, and accordingly the ratio B/G becomes large.

When the optical dome 10b makes a contact with the living tissue, the controller 26 sets the special light observation mode M2. When the optical dome 10b does not make a contact with the living tissue, the controller 26 sets the normal light observation mode M1. When the optical dome 10b makes a contact with the living tissue, the contact image capturing mode M3 may be alternatively set furthermore as described above.

Information on Distance: Magnetic Field Information

Figure 17:
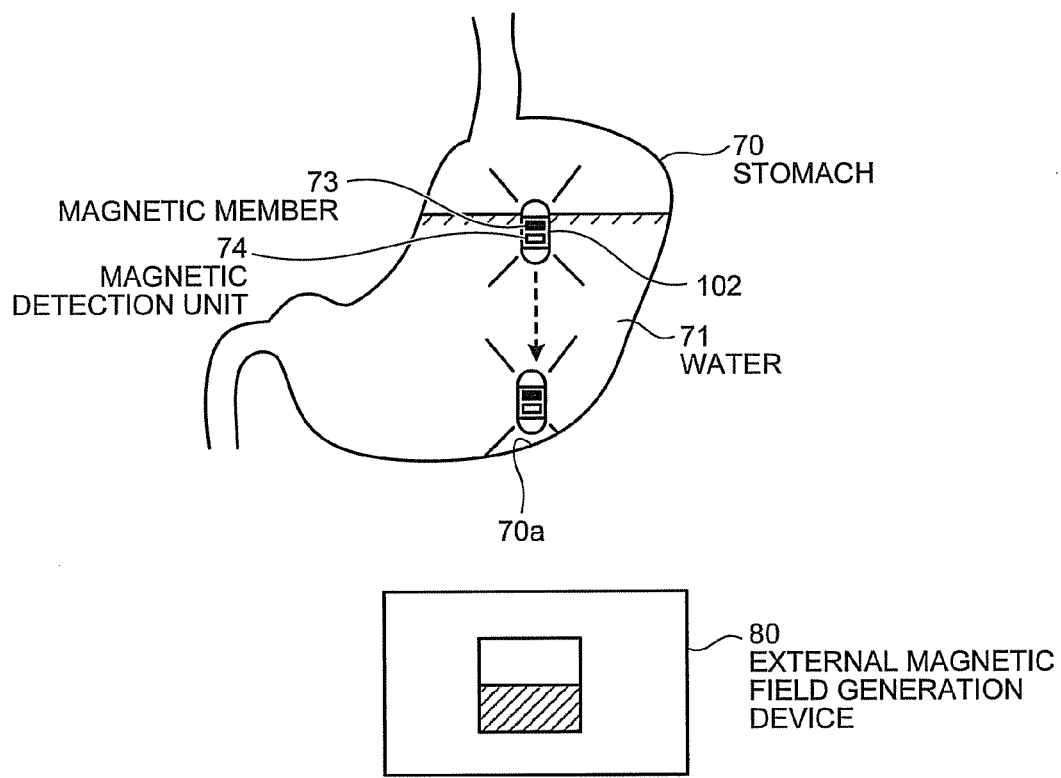
FIG. 17 is a schematic diagram of another example of the capsule endoscope device of the present invention and of an example in which a magnetic field from an external magnetic field generation device is applied to the capsule endoscope device in order to move the capsule endoscope device.

Here, magnetic information is used as the information on the distance. As depicted in FIG. 17, a binocular capsule endoscope 102 replaces the capsule endoscope 2 and the capsule endoscope 102 includes a magnetic member 73 and a magnetic detection unit 74 that detects a magnetic field. An external magnetic field generation device 80 is provided outside the subject 1 and generates a magnetic field to the capsule endoscope 102 that floats in water 71 in a stomach 70. By varying the magnetic field, the capsule endoscope 102 is attracted vertically downward and thus it can be moved in the vertical direction.

By detecting the size of the magnetic field from the magnetic detection unit 74 via the controller 26, the distance detection unit 22 can detect the distance between the capsule endoscope 102 and a tissue surface 70a of the stomach 70, which is an object. The controller 26 can perform the above-described process for changing and setting the image capturing mode according to the result of the detection.

Modification of Normal Light Observation Mode

In the above-described normal light observation mode, the normal light emitting devices LA and the special light emitting devices LB are caused to emit light simultaneously. Alternatively, in the normal light observation mode, only the normal light emitting devices LA may emit light. In other words, only the normal light emitting devices LA may be caused to emit light in the normal light observation mode and only the special light emitting devices LB may be caused to emit light in the special light observation mode.

Modification of Light Emitting Device

In the light emitting device 29, each of the normal light emitting devices LA and the special light emitting devices LB is formed as an independent light emitting device. Alternatively, the normal light emitting device LA and the special light emitting device LB may be formed as an integrated LED.

Figure 18:
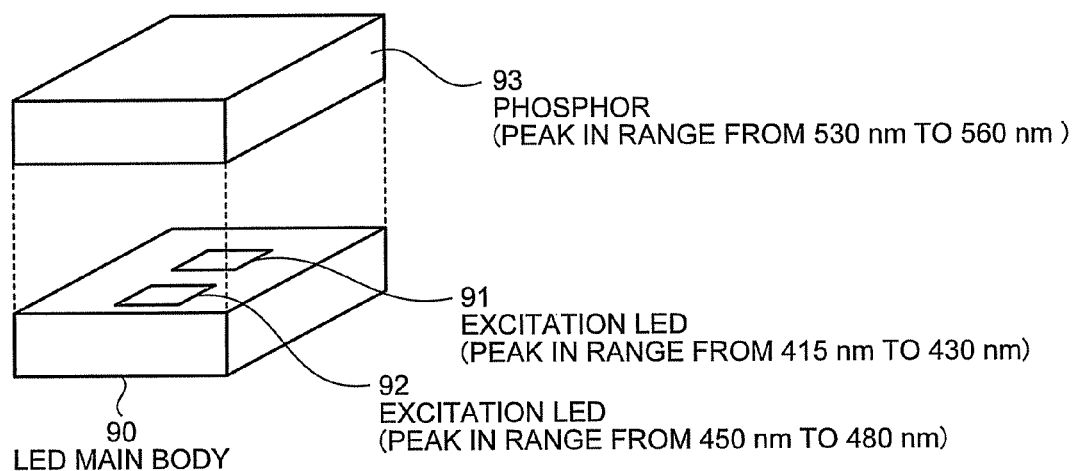
FIG. 18 is an exploded perspective view of an example of a light emitting device including a normal light emitting device and a special light emitting device that are formed as a pair, out of light emitting devices that are provided in the capsule endoscope device of the present invention.

For example, as depicted in FIG. 18, an integrated LED is realized in a way that an excitation LED 91 having a peak wavelength in a range from 415 nm to 430 nm and an excitation LED 92 having a peak in a range from 450 nm to 480 nm are formed in an LED main body 90 and a phosphor 93 having a fluorescent peak in a range from 530 nm to 560 nm is placed on and connected to the top portion of the LED main body 90. Thus, it is unnecessary to consider uniform arrangement of the normal light emitting deices LA and the special light emitting devices LB and accordingly the light emitting devices can be arranged easily and flexibly.

Figure 19:
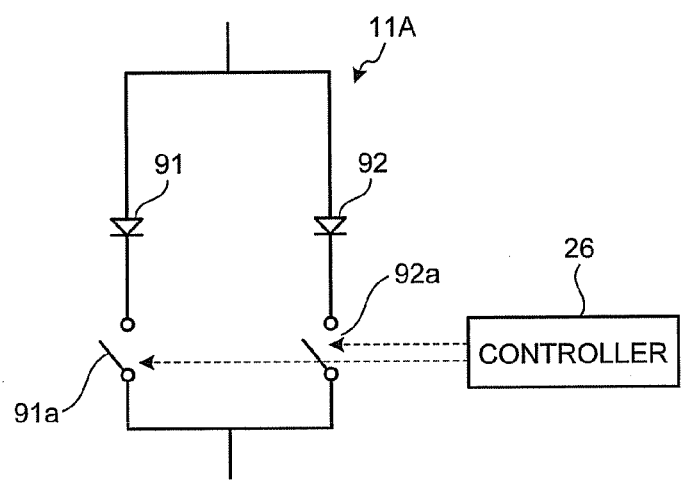
FIG. 19 is a circuit diagram of an example of a light emitting device drive circuit for the light emitting device in FIG. 18, out of light emitting device drive circuits that are provided in the capsule endoscope device of the present invention.

The same function as that of the special light emitting device LB can be achieved by causing the excitation LED 91 to emit light, and the same function as that of the normal light emitting device LA can be achieved by causing the excitation LED 92 to emit light. In this case, as depicted in FIG. 19, a light emitting device driver 11A is achieved by connecting the excitation LEDs 91 and 92 in parallel and providing a switch 91a connected in series with the excitation LED 91 and a switch 92a connected in series with the excitation LED 92. The controller 26 performs selective drive control to allow an arbitrary combination of light emission. Variable resistors (not shown) may be respectively connected in series with the excitation LEDs 91 and 92 such that the current ratio in the excitation LEDs 91 and 92 can be changed. In other words, the luminance intensity may be changed not only by on/off of the switches 91a and 92a but also in an analog manner. In addition to the two excitation LEDs 91 and 92, for example, an excitation LED having a peak wavelength of 400 nm may be further provided. In other words, instead of two excitation LEDs 91 and 92, three or more excitation LEDs may be used.

Color Component Adjustment on Light Emitting Device and Imaging Device

Here, the ratio regarding the excitation light wavelength components of the normal light emitting devices LA and the emission wavelength components of the phosphor and the ratio regarding the excitation light wavelength components of the special light emitting devices LB and the emission wavelength components of the phosphor are set uniform such that the ratio of white balance correction value for image processing is uniform.

Figure 20:
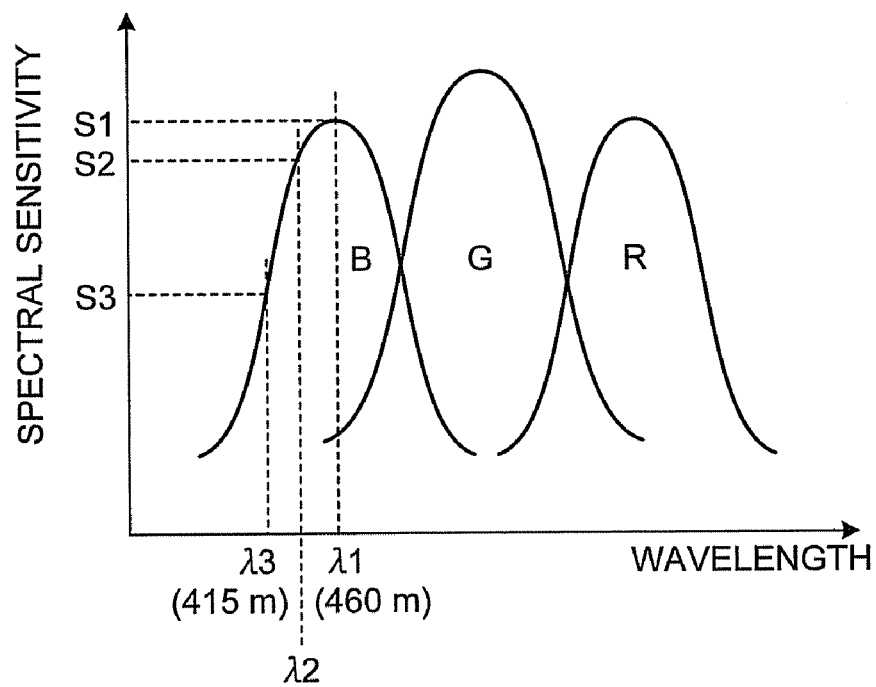
FIG. 20 is a graph of an example of spectral sensitivity spectrum of the imaging device in the capsule endoscope device of the present invention.

As depicted in FIG. 20, even with respect to an LED having the excitation light emission intensity with the same peak value at a wavelength $\lambda 1$ (460 nm) and a wavelength $\lambda 3$ (415 nm), the final received light intensity varies depending on the spectral sensitivity characteristics of the imaging device ($\lambda 3 < \lambda 2 < \lambda 1$). In other words, because the spectral sensitivity S3 of the imaging device with respect to the wavelength $\lambda 3$ is smaller than the spectral sensitivity S1 of the imaging device with respect to the wavelength $\lambda 1$, the final received light intensity with respect to the wavelength $\lambda 3$ is smaller than the received light intensity with respect to the wavelength $\lambda 1$ (S3<S2<S1). Accordingly, the light receiving intensities results in different spectra.

Figure 21:
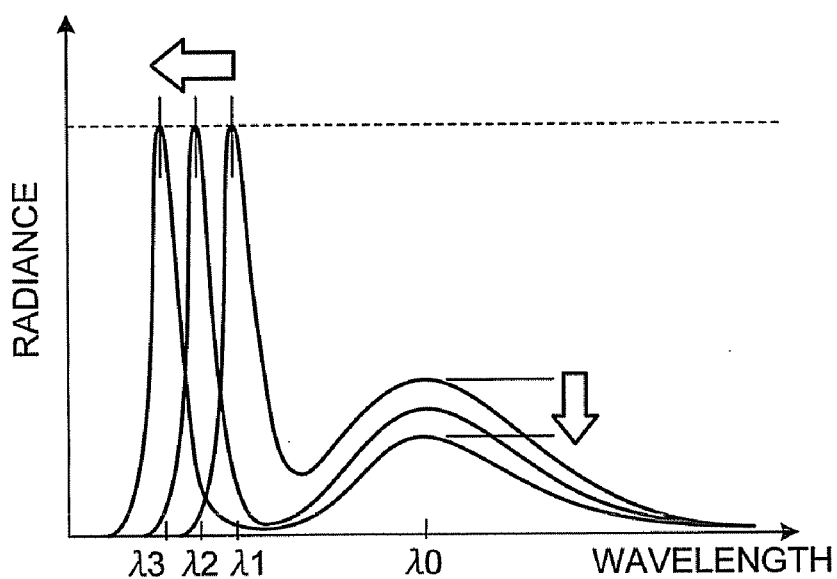
FIG. 21 is a graph of an example of luminance spectrum in a case in which the radiance of excitation light wavelength of each light emitting device in the capsule endoscope device of the present invention is set uniform and the spectral distribution of light emitted from a phosphor in each light emitting device is varied so that the received light intensity in the imaging device is set uniform between the image capturing modes.
Figure 22:
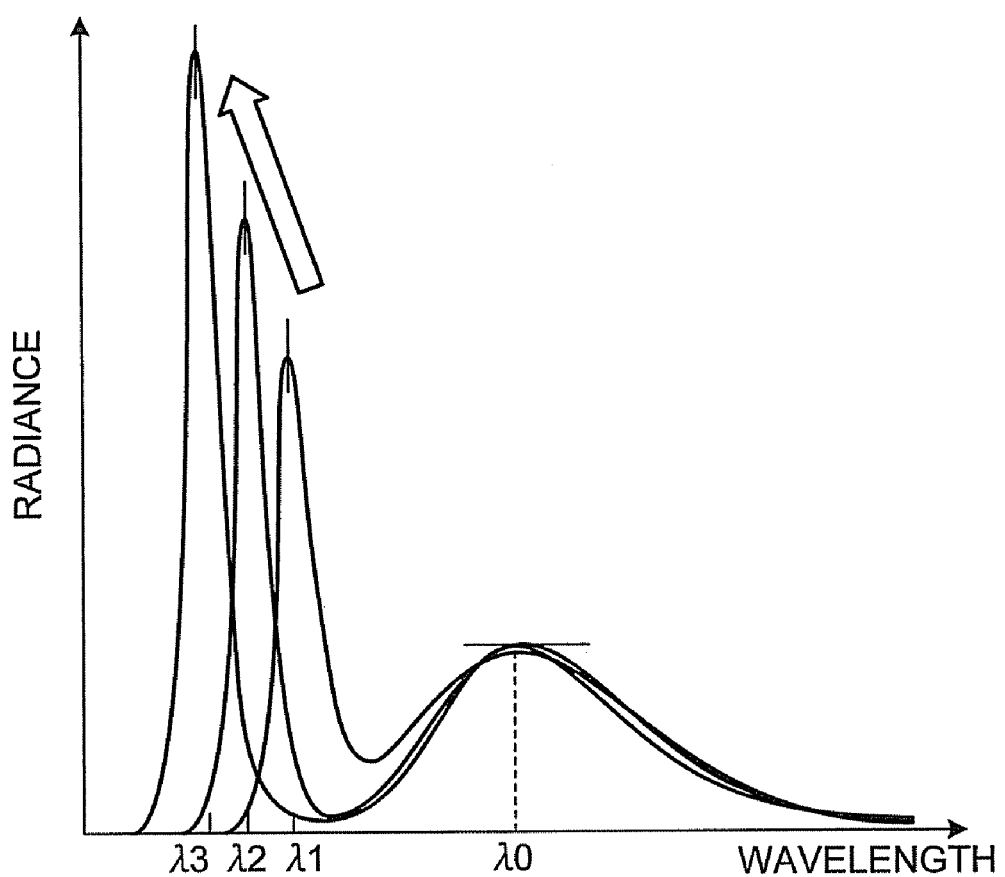
FIG. 22 is a graph of an example of luminance spectrum in a case in which the radiance around the peak wavelength of light emitted from the phosphor in each light emitting device in the capsule endoscope device of the present invention is set almost the same and, the shorter the peak wavelength is, the higher the peak radiance of each light emitting device is set, so that the received light intensity in the imaging device is set uniform between the image capturing modes.

For this reason, as depicted in FIG. 21, the peak radiances with respect to the wavelengths $\lambda 1$ and $\lambda 3$ are set equal such that the emission component ratio of the phosphor is reduced according to the spectral sensitivity characteristics of the B pixels of the imaging device. In other words, the material of the emission components of the phosphor is reduced such that the radiance of the emission components of the phosphor with respect to the peak wavelength $\lambda 0$ (560 nm) in FIG. 21 decreases according to a decrease in the spectral sensitivity characteristics of the B pixels. Accordingly, even with the same peak value with respect to the wavelength $\lambda 1$ and the wavelength $\lambda 2$, the final received light intensity spectra from the light emitting devices is in the uniform shape.

Alternatively, the material of the emission components of the phosphor may be set such that the values of radiance with respect to about the peak wavelength $\lambda 0$ of the emission components of the phosphor is uniform, and the peak radiance with respect to the wavelength $\lambda 3$ may be set larger than the peak radiance with respect to the wavelength $\lambda 1$ such that a decrease in the spectral sensitivity characteristics of the B pixels is corrected. Thus, the shape of the final received light intensity spectrum from each light emitting device is uniform.

For a detailed setting, specifically, an integral between the radiance characteristics of the normal light emitting device LA and the spectral sensitivity characteristics of the imaging device with respect to each of R, G, and B is obtained and specific values are set as ratios of the integrals (B/G, R/G). It is preferable that the ratio be about 1. In addition, an integral between the radiance characteristics of the normal light emitting device LB and the spectral sensitivity characteristics of the imaging device with respect to each of R, G, and B is obtained and ratio of the integrals are set as in the case of the normal light emitting device LA.

Alternatively, for example, when an integral X between the radiance characteristics of the normal light emitting device LA and the spectral sensitivity characteristics of the imaging device is obtained with respect to the B components, an integral Y between the radiance characteristics of the normal light emitting device LB and the spectral sensitivity characteristics of the imaging device is obtained with respect to the B components, and a ratio $\alpha$ (=Y/X) is obtained, ratios $\alpha$ with respect to other G components and R components are set to be equal to the ratio $\alpha$ (=Y/X).

Accordingly, in both of the case when any of the light emitting device is caused to emit light and the case when multiple different light emitting devices are caused to emit light, the received light intensity spectrum is uniform and accordingly the white balance correction value in the image processing is uniform. Accordingly, the common white balance correction value is used in the image processing and thus the image processing can be performed easily. Particularly, even for images that are captured using different capsule endoscopes, this color component adjustment allows the image display device 4 to use a common white balance correction value, which reduces the load of image processing.

External Input of Information on Distance

The capsule endoscope 2 acquires the information on the distance in the above-described embodiment, but the present invention is not limited to this. The capsule endoscope 2 may receive information on the distance that is acquired by an external device. The received information on the distance is sent to the distance detection unit 22 via the controller 26.

Figure 23:
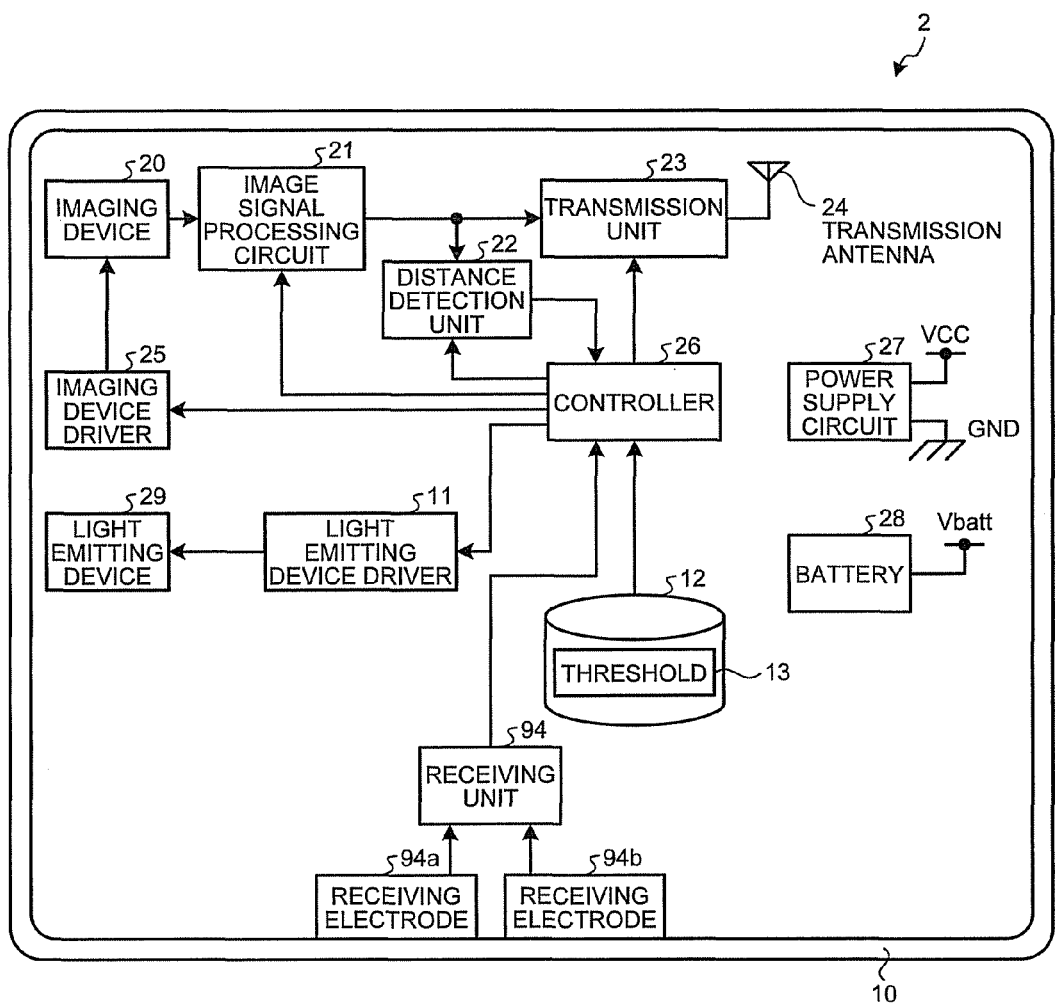
FIG. 23 is a diagram of a configuration example of a capsule endoscope device that can receive a signal from outside by in-vivo communications, out of capsule endoscope devices of the present invention.
Figure 24:
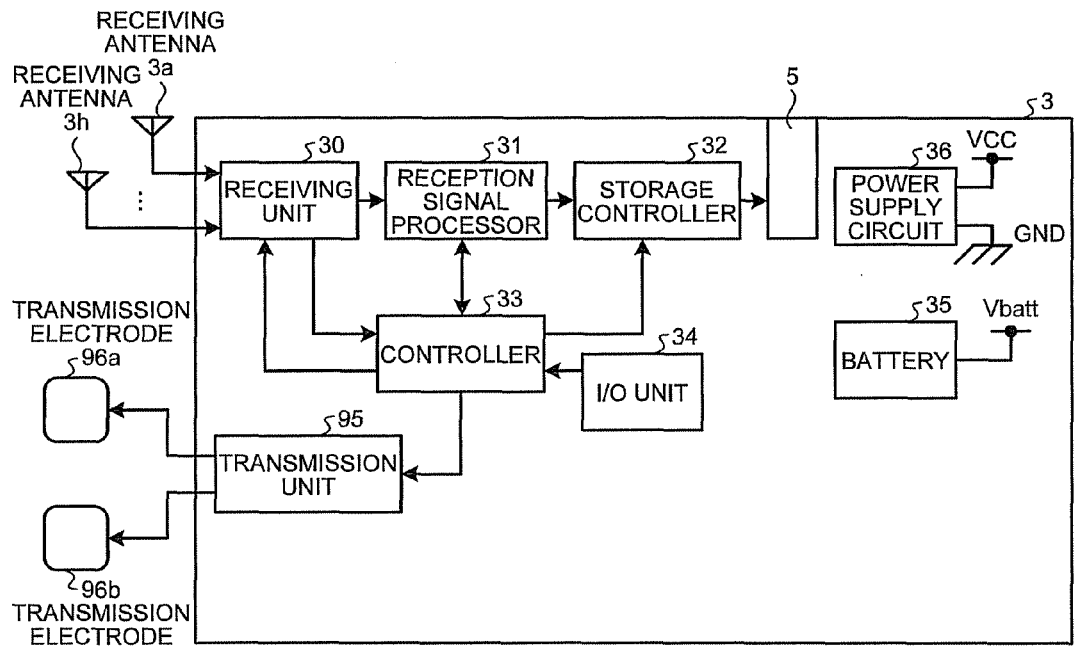
FIG. 24 is a diagram of a configuration example of a receiving device capable of transmission to the capsule endoscope device in FIG. 23 by in-vivo communications.

In this case, however, the capsule endoscope 2 needs to include a receiving mechanism and the receiving device 3 needs to include a transmission function. Thus, as depicted in FIG. 23, the capsule endoscope 2 is provided with a pair of receiving electrodes 94a and 94b for in-vivo communications and a receiving unit 94 that receives a reception signal from the potential difference between the receiving electrodes 94a and 94b. In contrast, as depicted in FIG. 24, the receiving device 3 is provided with a pair of transmission electrodes 96a and 96b and a transmission unit 95 that generates a potential difference between the transmission electrodes 96a and 96b and generates a transmission signal in the capsule endoscope 2 via the subject 1.

With the function of transmission from the receiving device 3 to the capsule endoscope 2, the receiving device 3 can analyze an image and transmit information on the distance, such as the above-described brightness of the image and the space frequency, based on the result of the analysis to the capsule endoscope 2. When the external magnetic field generation device is used, without providing the capsule endoscope 2 with a magnetic field detection unit, the image capturing mode can be switched as described above by transmitting the magnetic field generation information on the external magnetic field generation device and by using the magnetic field information as the information on the distance.

Information on Distance is Output to the Outside and Image Capturing Condition is Focal Distance The information on the distance is output to the operation unit of the capsule endoscope 2 in the above-described embodiment, but the information on the distance may be output to the outside of the capsule endoscope 2. For example the information on the distance may be output to an operation unit of the receiving device 3 or an operation unit of the image processing device 4.

In this case, instead of the capsule endoscope 2, a binocular capsule endoscope 202 may be used that includes two imaging systems A and B respectively having different focal distances, includes a magnet 210, and that can be reversed using an external magnetic field. The capsule endoscope 202 includes optical domes 210a and 210b corresponding to the optical dome 10b on both ends in the longitudinal direction. The imaging system A having a long focal distance is provided on one end and the imaging system B having a short focal distance is provided on the other end. A battery 231, the magnet 210, and a transmission antenna 250 are mounted between the imaging systems A and B. In the imaging systems A and B, light emitting devices 229a and 229b are arranged annularly around lenses 221a and 221b on control substrates 230a and 230b, respectively. Because the weight of the battery 231 is large, a ballast 240 serving as a weight member is provided on the opposite side with respect to the battery 231 such that the capsule gravitational center G of the capsule endoscope 202 is positioned at the center of the capsule endoscope 202.

Figure 26:
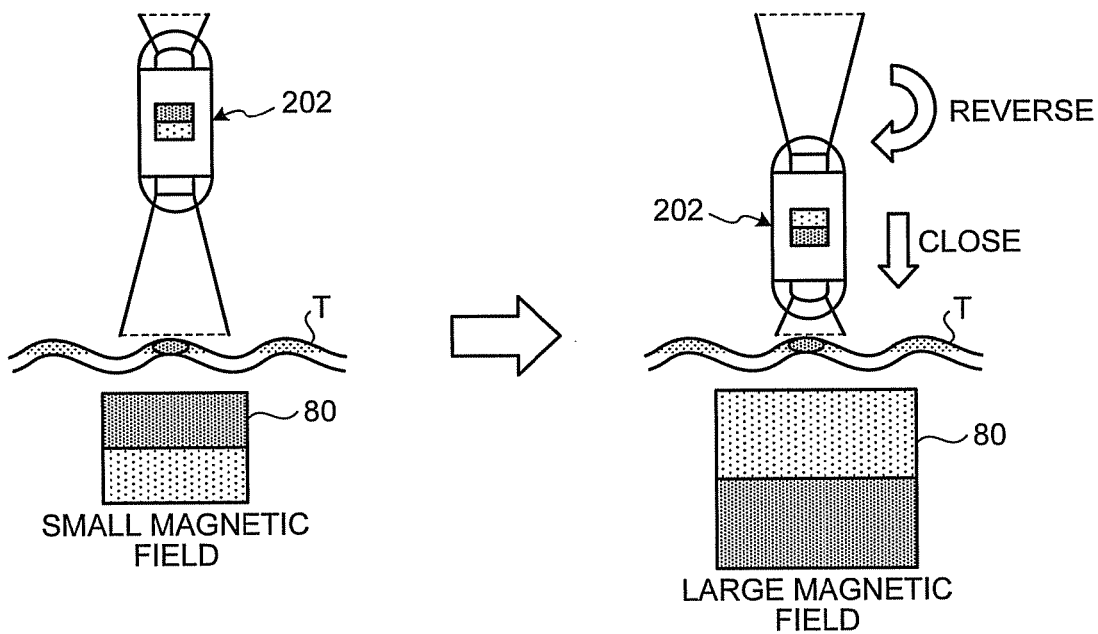
FIG. 26 is a diagram of a state in which magnetic guidance and reverse processing are performed on the capsule endoscope device in FIG. 25.

Because the capsule gravitational center G is positioned at the center, the capsule endoscope 202 can easily rotate in liquid. By applying a magnetic field using the external magnetic field generation device 80 illustrated in FIG. 17, the capsule endoscope 202 can be easily rotated. When the information on the distance is output from the capsule endoscope 202 to the external magnetic field generation device 80, the external magnetic field generation device 80 controls the orientation of the magnetic field to be generated on the basis of the information on the distance, which is input. When the distance is short, the external magnetic field generation device 80 orients the imaging system B having a short focal distance toward an in-vivo tissue T, which is an object. When the distance is long, the external magnetic field generation device 80 orients the imaging system A having a long focal distance toward the in-vivo tissue T, which is an object (see FIG. 26).

The image capturing condition is changed by changing the image capturing mode in the above-described embodiment, but the image capturing condition is changed here by selecting an imaging system having a focal distance corresponding to the distance. The operation unit serves as a magnetic field generation controller of the external magnetic field generation device 80.

Image Capturing Condition: Focal Distance

Figure 25:
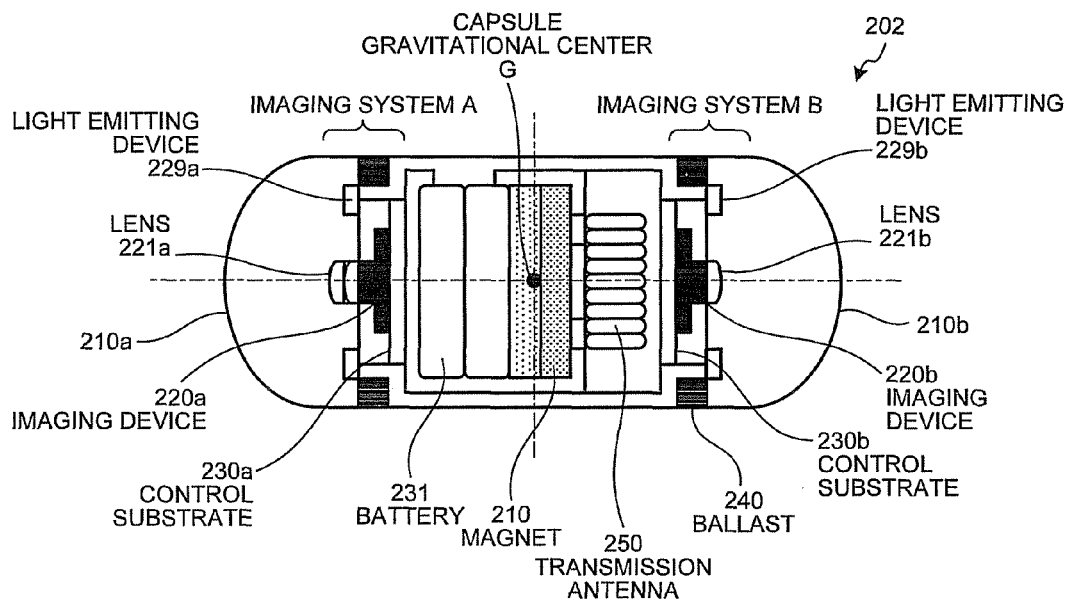
FIG. 25 is a diagram of a configuration example of a capsule endoscope device including two image capturing systems, out of the capsule endoscope devices of the present invention.
Figure 27:
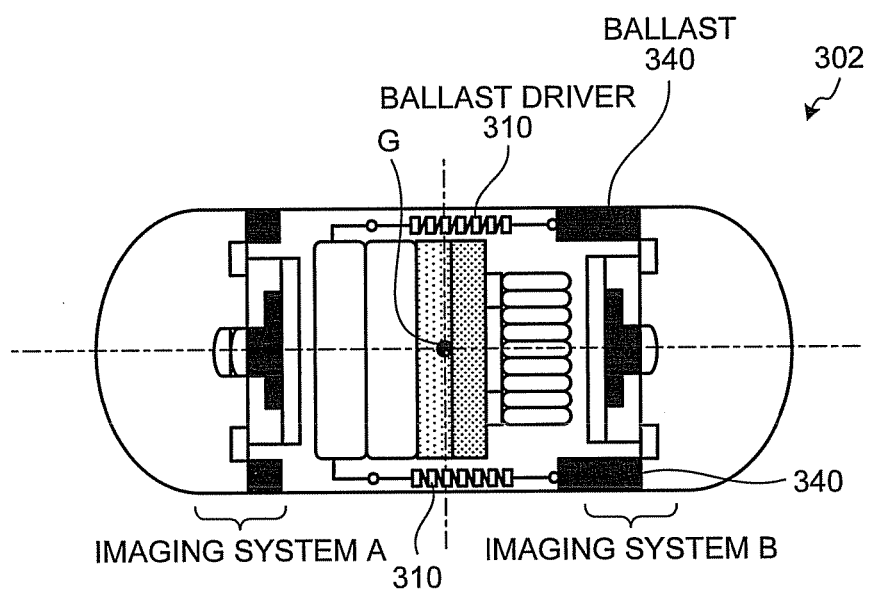
FIG. 27 is a diagram of a configuration of a capsule endoscope device including two image capturing systems and having a function for shifting the center of gravity, out of capsule endoscope devices of the present invention.

The imaging systems having different focal distances may be switched as the image capturing condition as described above by changing the gravity center position of the capsule endoscope without a magnetic field. For example, as depicted in FIG. 27, a capsule endoscope 302 includes a movable ballast 340 in place of the fixed ballast 240 of the capsule endoscope 202 and includes a ballast driver 310 that drives the ballast 340 to move. The configuration other than these aspects is the same as that of the capsule endoscope 202 in FIG. 25.

The ballast driver 310 is formed of SMA (shape memory alloy) that compresses and extends in the longitudinal direction. By applying a current to the SMA, the SMA compresses or extends and thus moves the ballast 340, thereby changing the position of the capsule gravity center G. By changing the position of the capsule gravity center G, the capsule endoscope 302 can be rotated and thus an imaging system can be selected according to the information on the distance. In other words, in this case, the operation unit serves as the ballast driver 310 of the capsule endoscope 302 and thus the image capturing condition is the above-described focal distance.

Modification 1 of Color Filter

Figure 28A:
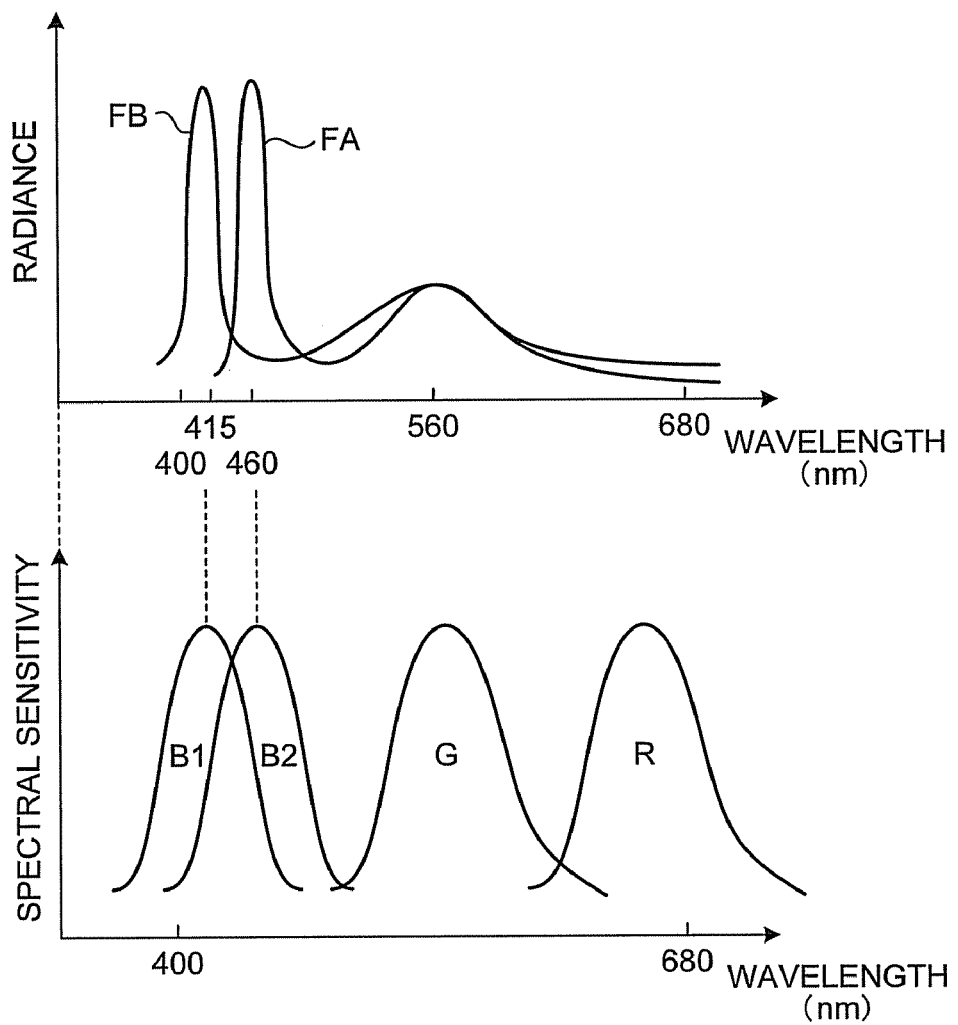
FIG. 28A is a graph of another example of the radiance spectrum of the light emitting device and the spectral sensitivity spectrum of the imaging device in the capsule endoscope device of the present invention.
Figure 28B:
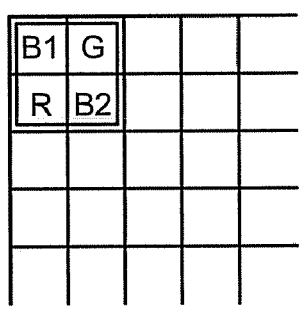
FIG. 28B is a diagram of an example of an arrangement of color filters in the imaging device having the spectral sensitivity spectrum in FIG. 28A.

It is assumed that a Bayer arrangement of color filters is used in the above-described embodiment, but a captured image is obtained here using color filters in a changed configuration. In other words, the luminance spectrum FA by the normal light emitting device LA and the luminance spectrum FB by the special light emitting device LB, depicted in FIG. 28A, are obtained. Four pixels of R, G, B1, and B2 are used for a color filter and the pixel B1 and the pixel B2 are arranged diagonally. As depicted in FIG. 28A, the spectral sensitivity of the pixel B1 corresponds to the excitation light spectrum of the special light emitting device LB and the spectral sensitivity of the pixel B2 corresponds to the excitation light spectrum of the normal light emitting device LA.

In the normal light image capturing mode, a normal light image is generated using R pixels, G pixels, and (B1+B2) pixels. In the special light image capturing mode, a special light image (blood absorbed light image) is generated using B2 pixels and G pixels. In this case, because the spectra of the spectral sensitivity of the B1 pixel and the G pixel are separated, a clear special light image can be obtained. The G components are absorbed in a relatively thick blood vessel positioned in a portion deeper than that of a blood vessel in which B1 (blue) components are absorbed and accordingly the two blood vessels can be separated.

Modification 2 of Color Filter

Figure 29A:
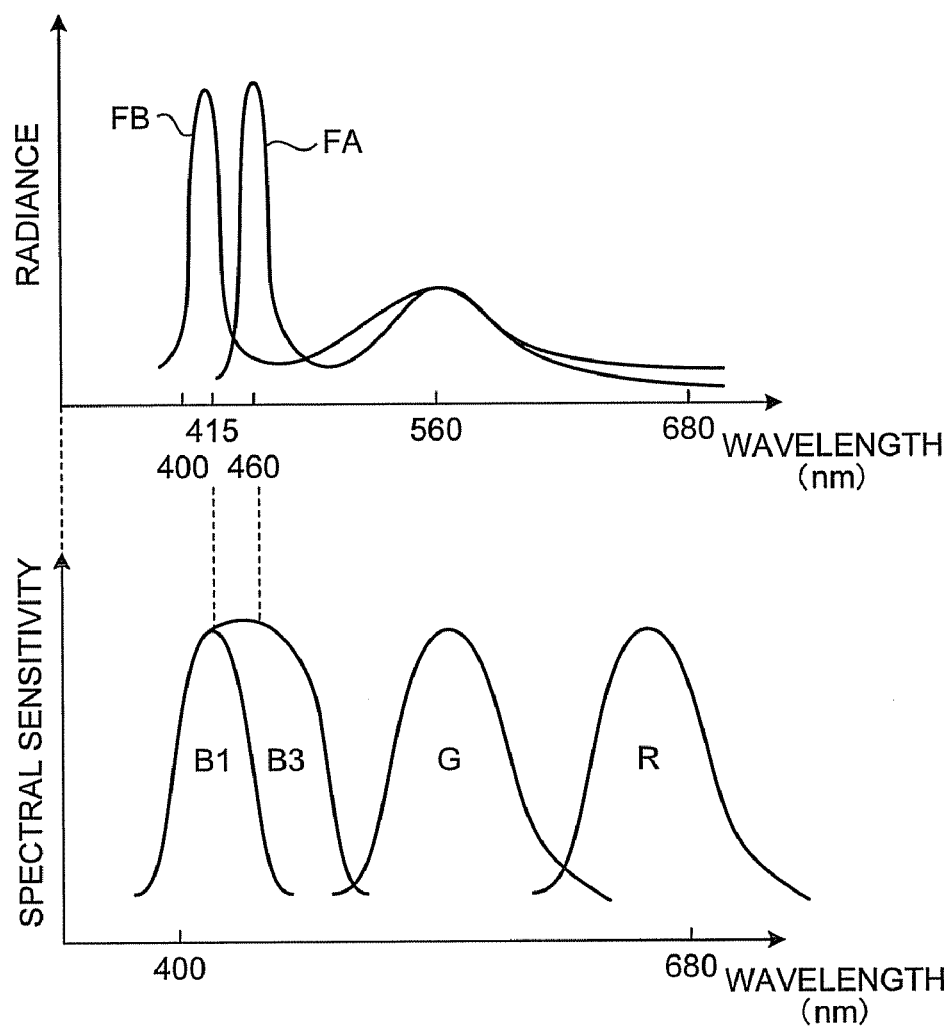
FIG. 29A is a graph of still another example of the radiance spectrum of the light emitting device and the spectral sensitivity spectrum of the imaging device in the capsule endoscope device of the present invention.
Figure 29B:
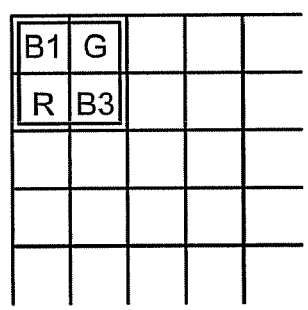
FIG. 29B is a diagram of an example of an arrangement of color filters in the imaging device having the spectral sensitivity spectrum in FIG. 29A.

In Modification 2, while the luminance spectrum FA by the normal light emitting device LA and the luminance spectrum LB by the special light emitting device FB similar to those of Modification 1 are obtained (see FIG. 29A), the luminance spectrum of a pixel B3 overlaps the luminance spectrum of the pixel B1 in Modification 1 (see FIG. 29A). As depicted in FIG. 29B, four pixels of R, G, B1, and B3 are used for a color filter and the pixel B1 and the pixel B3 are arranged diagonally. In this case, as well, because the spectra of the spectral sensitivity of the B3 pixel and the G pixel are separated, a clear special light image can be obtained.

Modification 3 of Color Filter

Figure 30A:
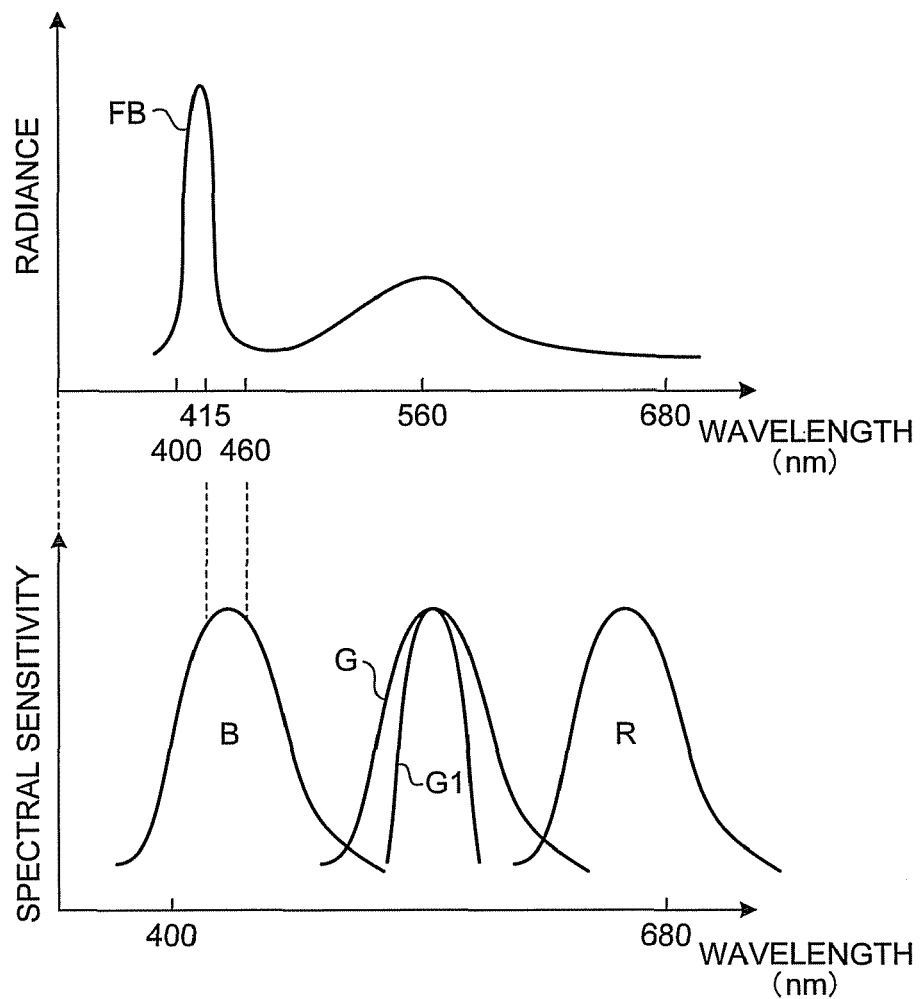
FIG. 30A is a graph of still another example of the radiance spectrum of the light emitting device and the spectral sensitivity spectrum of the imaging device in the capsule endoscope device of the present invention.
Figure 30B:
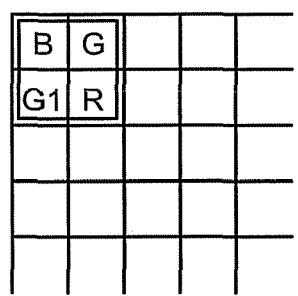
FIG. 30B is a diagram of an example of an arrangement of color filters in the imaging device having the spectral sensitivity spectrum in FIG. 30A.

In Modification 3, as depicted in FIGS. 30A and 30B, one of two G pixels in a Bayer arrangement serves as a G1 pixel having a spectral sensitivity spectrum in a narrow band. Here, B pixels and G1 pixels are used in the special light observation mode, and R pixels, G pixels (or G pixels and G1 pixels), and B pixels are used in the normal light observation mode. In this case, as well, because the spectra of the spectral sensitivity of the B pixel and the G1 pixel are separated, a clear special light image can be obtained. FIG. 30A also depicts the luminance spectrum FB by the special light emitting device LB.

Modification 1 of Imaging System

Figure 31:
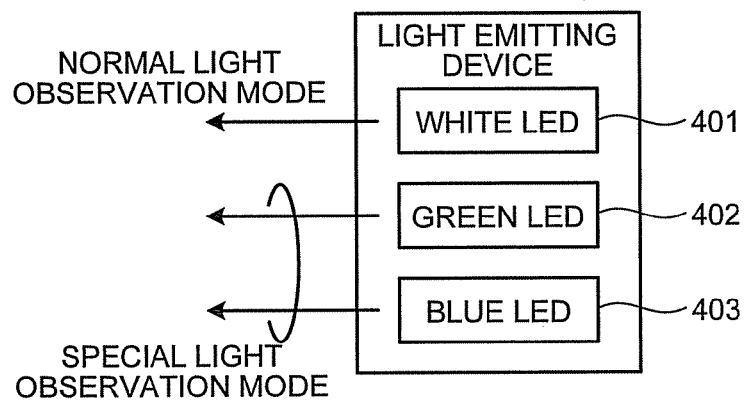
FIG. 31 is a diagram of a configuration of a modification of the light emitting device of the capsule endoscope device of the present invention.

In the above-described embodiment, the normal light emitting devices LA and the special light emitting devices LB are used to obtain a normal light image and a special light image. Here, as depicted in FIG. 31, three LEDs, i.e., a white LED 401 that emits white light, a green LED 402 that emits green light, and a blue LED 403 that emits blue light are provided without a phosphor. In the normal observation mode, only the white LED 401 is caused to emit light. In the special light observation mode, the green LED 402 and the blue LED 403 are caused to emit light.

Figure 32A:
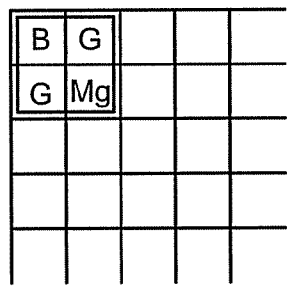
FIG. 32A is a diagram of a configuration of an example of a color filter corresponding to the light emitting device in FIG. 31.
Figure 32B:
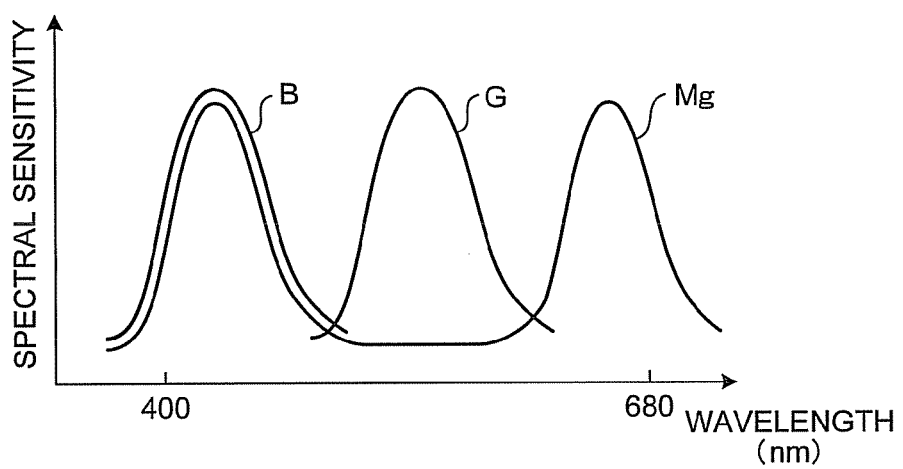
FIG. 32B is a graph of an example of a spectral sensitivity spectrum of the imaging device including the color filter in FIG. 32A.

For the color filter in this case, as depicted in FIG. 32A, Mg (magenta) pixels are used instead of R pixels in a Bayer arrangement. Regarding the spectral sensitivity spectra in this case, as represented in FIG. 32B, the Mg pixel has the spectral sensitivity spectra covering those of the R pixel component and the B pixel component. In the normal observation mode, by outputting, as R pixel components, components obtained by subtracting the B pixel components from the Mg pixel components, an RGB normal light image can be obtained. In contrast, in the special light observation mode, because only the green LED 402 and the blue LED 403 are cause to emit light, no light of R components is emitted. The B components can have doubled received light intensity of that of the B pixels because of a B pixel component area of the B pixel component and the Mg pixel component, and the G components can have doubled received light intensity because of two G pixels. Thus, doubled light receiving intensity of that with a Bayer arrangement can be obtained using one pixel array. Accordingly, a special light image with a high resolution can be obtained.

Modification 2 of Imaging System

Figure 33A:
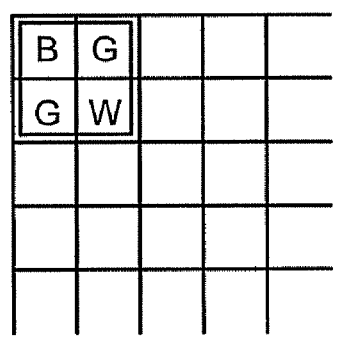
FIG. 33A is a diagram of a configuration of another example of the color filter corresponding to the light emitting device in FIG. 31.
Figure 33B:
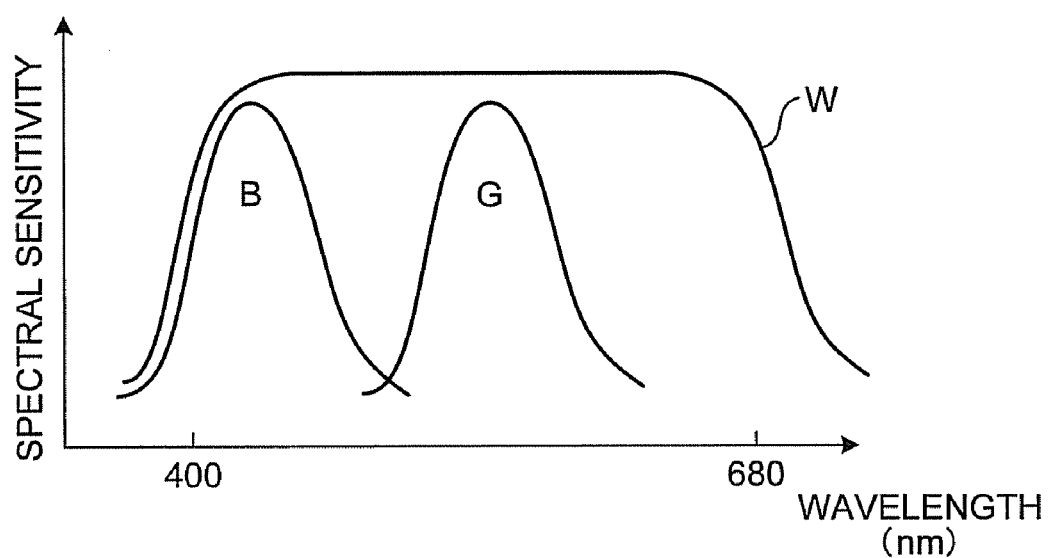
FIG. 33B is a graph of an example of a spectral sensitivity spectrum of the imaging device including the color filter in FIG. 33A.

A high-resolution special light image can be obtained using the light emitting device in FIG. 31 having the color filter arrangement in FIG. 33A. In other words, a W (white) pixel is provided instead of an R pixel in the Bayer arrangement. As depicted in FIG. 33B, the W pixel has the spectral sensitivity spectrum covering the whole RGB area. In Modification 2, different from Modification 1, in the normal light observation mode, all of the white LED 401, the green LED 402, and the blue LED 403 are caused to emit light, and R components are generated by subtracting a sum of B pixel components and G pixel components from the W pixel components. In contrast, in the special light observation mode, as in the case of Modification 1, the green LED 402 and the blue LED 403 are cause to emit light. The B components can have doubled received light intensity of the B pixels because of the B pixel components and B components of the W pixel components, the G components can have doubled received light intensity because of two G pixels. Thus, in the special light observation mode, doubled light receiving intensity can be obtained and accordingly a high-resolution special light image can be obtained.

Output of Additional Image Capturing Mode Information

Figure 34:
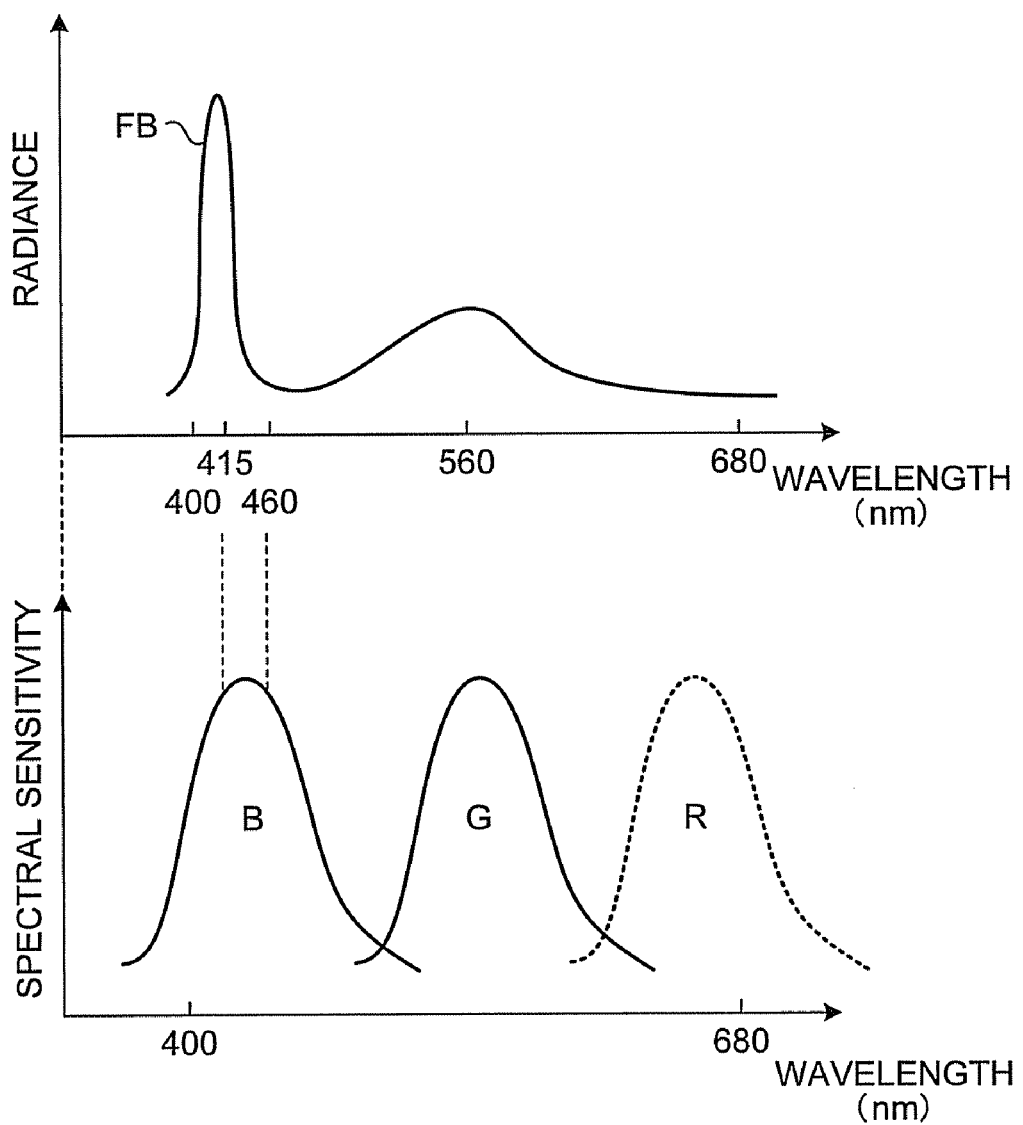
FIG. 34 is a graph of still another example of the radiance spectrum of the special light emitting device and the spectral sensitivity spectrum of the imaging device in the capsule endoscope device of the present invention.

In the case of the spectral sensitivity spectrum in FIG. 34 in a normal Bayer arrangement, when obtaining an image using illumination by only the special light emitting devices LB having the luminance spectrum FB in FIG. 34, a normal light image can be obtained using RGB components and a special light image can be obtained using only GB components without R components. In other words, a normal light image and a special light image can be obtained when the special light emitting devices LB are used; therefore, it is preferable that, when the image display device 4 outputs and displays images, image processing for obtaining a normal light image and a special light image or display processing for displaying a normal light image and a special light image be performed. A normal light image can be obtained when only the normal light emitting devices LA are used or when the normal light emitting devices LA and the special light emitting devices LB are used.

Figure 35:
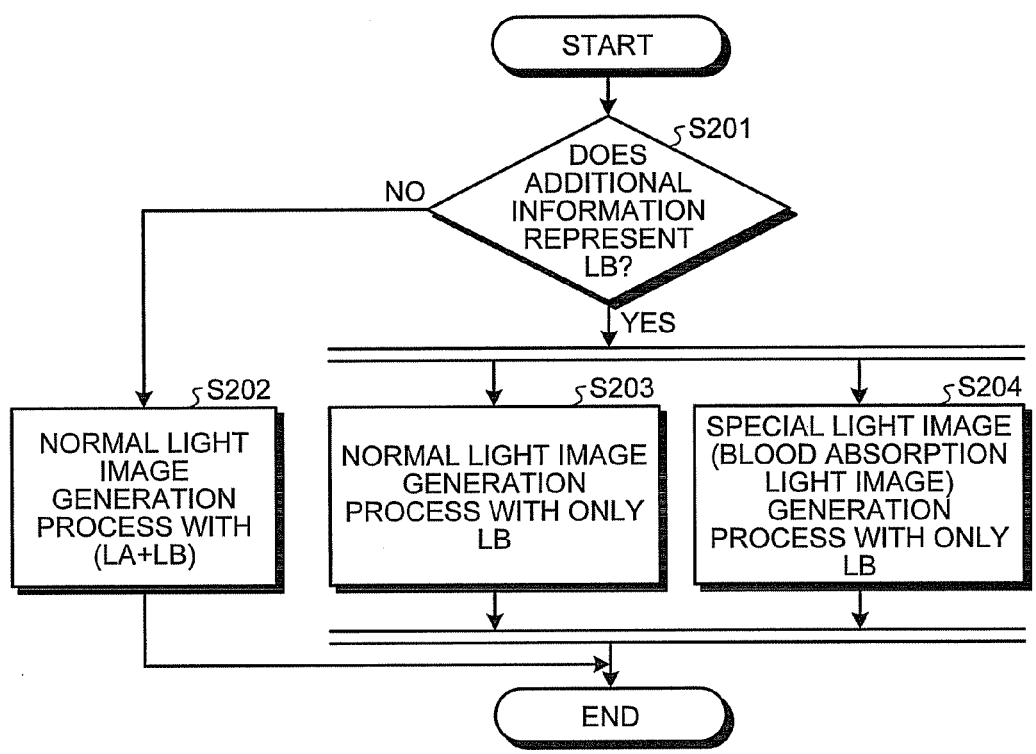
FIG. 35 is a flowchart of an example of a procedure of image processing performed by the image display device in the capsule endoscope system in FIG. 1.
Figure 36:
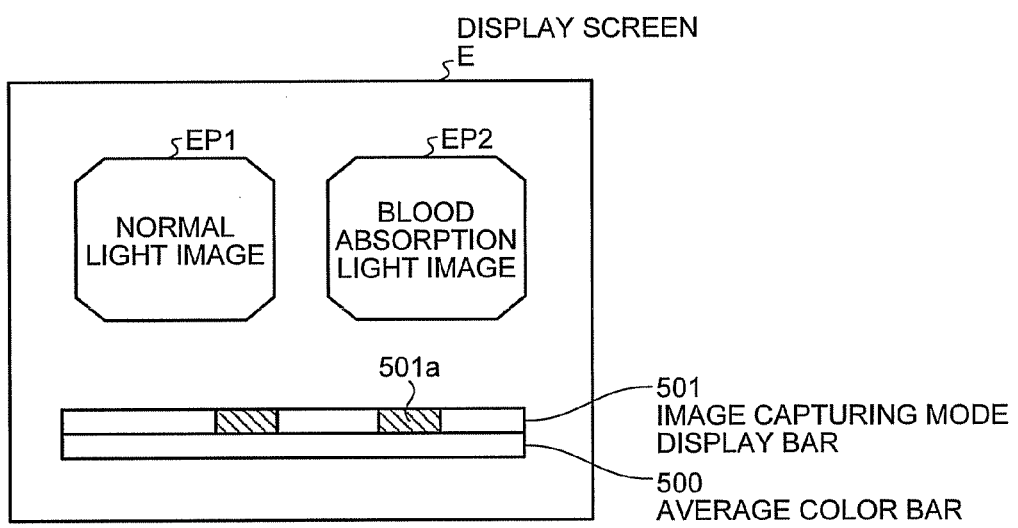
FIG. 36 is a diagram of an example of a display screen of the image display device in the capsule endoscope system in FIG. 1.

The capsule endoscope 2 transmits the image capturing mode information, which represents the image capturing condition, as additional information contained in the imaging information. When displaying each image, the image display device 4 that receives the imaging information performs image processing on each image according to the process procedure in FIG. 35. Specifically, first, it is determined whether the additional information corresponding to an image represents that the image is captured using only the special light emitting devices LB (step S201). When the additional information represents that the image is not captured using only the special light emitting device LB (NO at step S201), a process for generating a normal light image, which is captured when the normal light emitting devices LA and the special light emitting devices LB, including a normal light image that is captured using only the normal light emitting devices LA, is performed (step S202) and the process ends.

In contrast, when the additional information represents only the special light emitting devices LB (YES at step S201), the normal light image generation process for an image that is captured using only the special light emitting devices LB is performed (step S203) in parallel with a special light image (blood absorption light image) generation process for an image that is captured in only the special light emitting device LB observation mode (step S204) and the process ends.

The normal light image and the special light image (blood absorption light image) can be displayed in areas EP1 and EP2, respectively, on a display screen E of the monitor 44. On the display screen E, an average color bar 500 is displayed in which a series of image groups are arranged according to the characteristic colors in the order the images are acquired. The average color bar 500 is a GUI (graphical user interface). BY pointing a desired position on the average color bar 500, an image corresponding to the desired position is output and displayed or images are sequentially output and displayed and from the image corresponding to the desired position. If there are special light images, an image capturing mode display bar 501, connected to the top part of the average color bar 500, for outputting and displaying an area 501a of images is provided in the same order the images are acquired. The area 501a on the image capturing mode display bar 501 represents that special light image can be displayed in addition to the display of normal light images. If all the images are captured using only the special light emitting devices LB, the area 501a on the image capturing mode display bar 501 can be output and displayed as an area for which it is preferable that special light images be displayed. Determination on the preferability of the area is made according to the information on the distance added to the imaging information or the determination result based on the information on the distance. When the distance is shorter than a threshold, the area is displayed as an area with the preferability.

Modification of Image Capturing Mode

In the above-described embodiment, any one of the normal light observation mode or the special light observation mode is selected and set. The selected and set image capturing mode serves as the image capturing mode for the next image capturing. Setting and changing of the image capturing mode may be performed from the chronological point of view. For example, an alternate image capturing mode, in which the normal light observation mode and the special light observation mode are used alternately according to the image capturing condition, and a temporary image capturing mode, in which an image capturing mode that is selected and set temporarily as an interrupt is performed only once, may be provided.

In the drawings corresponding to the embodiment and the drawings corresponding to the modifications, provision of hatching to the cross-sectional views is omitted properly.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule endoscope device comprising:
    an illumination unit that includes at least a white light illumination unit that emits white light and a special light illumination unit that emits specific visible light components, the illumination unit illuminating a living tissue using at least one of the white light illumination unit and the special light illumination unit;
an imaging unit that captures an image of the living tissue, the imaging unit comprising a plurality of imaging systems having different focal distances;
a transmission unit that transmits imaging information containing the image captured by the imaging unit;
a storage unit that stores a threshold with respect to information on a distance between the capsule endoscope device and the living tissue;
a detection unit that detects the information on the distance between the capsule endoscope device and the living tissue;
an adjustment unit that adjusts a position of the center of gravity of the capsule endoscope device; and
an output unit that compares the information on the distance detected by the detection unit with the threshold, wherein the output unit selects an image capturing condition for a special light observation mode that causes only the special light illumination unit to emit light if a result of the comparing indicates that the distance to the living tissue is not larger than the threshold, the output unit selects an image capturing condition of a normal light observation mode that causes at least the white light illumination unit to emit light if the result of the comparing indicates that the distance to the living tissue is larger than the threshold, the output unit outputs the selected image capturing condition to an operation unit that relates to image capturing, the output unit selects based on the result of the comparing an image capturing condition for performing image capturing with the either of the imaging systems, and the output unit outputs the selected image capturing condition to the operation unit and causes the adjustment unit to perform an adjustment operation.

2. A capsule endoscope device comprising:
an illumination unit that includes at least a white light illumination unit that emits white light and a special light illumination unit that emits specific visible light components, the illumination unit illuminating a living tissue using at least one of the white light illumination unit and the special light illumination unit;
an imaging unit that captures an image of the living tissue;
a transmission unit that transmits imaging information containing the image captured by the imaging unit;
a storage unit that stores a threshold with respect to information on a distance between the capsule endoscope device and the living tissue;
a detection unit that detects the brightness of the image as the information on the distance between the capsule endoscope device and the living tissue; and
an output unit that detects whether the image is captured in an axial direction of a lumen based on the brightness of a peripheral portion area and a center portion area of the image captured by the imaging unit and the threshold, wherein the output unit selects an image capturing condition for a special light observation mode that causes only the special light illumination unit to emit light if the output unit detects that the image is not captured in the axial direction of the lumen, the output unit selects an image capturing condition of a normal light observation mode that causes at least the white light illumination unit to emit light if the output unit detects that the image is captured in the axial direction of the lumen, and the output unit outputs the selected image capturing condition to an operation unit that relates to image capturing.

3. The capsule endoscope device according to claim 2, wherein the output unit detects that the image is captured in the axial direction of the lumen if the brightness of the center portion area is less than a first threshold and the brightness of the peripheral portion area is equal to or more than a second threshold.

* * * * *